United States Patent [19]

Kawasaki et al.

[11] Patent Number: 5,681,717
[45] Date of Patent: Oct. 28, 1997

[54] DNA ENCODING NOVEL CELL SURFACE PROTEIN

[75] Inventors: Hisashi Kawasaki; Makoto Tsuchiya; Kiyoshi Miwa; Yoshio Kawahara, all of Kawasaki, Japan

[73] Assignee: Ajinomoto Co., Inc., Tokyo, Japan

[21] Appl. No.: 633,485

[22] Filed: Apr. 17, 1996

Related U.S. Application Data

[62] Division of Ser. No. 295,670, filed as PCT/JP94/00039 Jan. 13, 1994, Pat. No. 5,547,864.

[30] Foreign Application Priority Data

Jan. 13, 1993 [JP] Japan ................................ 5-004069

[51] Int. Cl.[6] .............................. C12P 21/06; C12P 13/04; C12P 1/04; C07H 21/04
[52] U.S. Cl. ..................... 435/69.1; 435/106; 435/170; 435/252.32; 435/320.1; 536/23.7
[58] Field of Search ..................... 435/170, 106, 435/252.32, 320.1, 69.1; 536/23.7

[56] References Cited

FOREIGN PATENT DOCUMENTS

| 2667875 | 4/1992 | France . |
|---|---|---|
| 57-22558 | 2/1982 | Japan . |
| 57-134500 | 8/1982 | Japan . |
| 57-183799 | 11/1982 | Japan . |
| 58-35197 | 3/1983 | Japan . |
| 58-67699 | 4/1983 | Japan . |
| 58-192900 | 11/1983 | Japan . |
| 2-109985 | 4/1990 | Japan . |
| 2-207791 | 8/1990 | Japan . |
| 4-271780 | 9/1992 | Japan . |

OTHER PUBLICATIONS

Peyret, J.L. (1983) "Characterization of the cspβ gene encoding PS2, an ordered surface-layer protein in *Corynebacterium glutamicum*" *Mol. Microbiol*, 9(1):97–109.

*Primary Examiner*—Robert A. Wax
*Assistant Examiner*—Kawai Lau
*Attorney, Agent, or Firm*—Oblon, Spivak, McClelland, Maier & Neustadt, P.C.

[57] ABSTRACT

A DNA fragment containing a gene coding for a novel cell surface layer protein derived from *Brevibacterium lactofermentum* and having two sequences of:

(1)Thr—Leu—Arg—Gln—His—Tyr—Ser—Ser—Leu—Ile—Pro—Asn—Leu—Phe—Ile—Ala—Ala—Val—Gly—Asn—Ile—Asn—Glu—Leu—Asn—Asn—Ala—Asp—Gln—Ala—Ala—Arg—Glu—Leu—Phe—Leu—Asp—Trp—Asp—Thr (SEQ ID NO:1) and:
(2)Asn—Lys—Thr—Asp—Phe—Ala—Glu—Ile—Glu—Leu—Tyr—Asp—Val—Leu—Tyr—Thr—Asp—Ala—Asp—Ile—Ser—Gly—Asp—Ala—Pro—Leu—Leu—Ala—Pro—Ala—Tyr—Lys (SEQ ID NO:2)

in the molecule, and having a molecular weight of about 63,000 dalton is introduced into Coryneform bacteria to obtain a transformant, or originate a mutant strain being sufficient in the novel cell surface layer protein, which is used for producing a useful substance such as an L-amino acid by an L-amino acid fermentation method.

5 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 40 amino acids
        ( B ) TYPE: amino acid
        ( C ) STRANDEDNESS: Not Relevant
        ( D ) TOPOLOGY: linear ( i i ) MOLECULE TYPE: protein ( v i ) ORIGINAL SOURCE:
        ( A ) ORGANISM: Brevibacterium lactofermentum
        ( B ) STRAIN: 2256 (ATCC 13869)

( x i ) SEQUENCE DESCRIPTION: SEQ ID NO:1:

```
Thr Leu Arg Gln His Tyr Ser Ser Leu Ile Pro Asn Leu Phe Ile Ala
 1               5                  10                  15

Ala Val Gly Asn Ile Asn Glu Leu Asn Asn Ala Asp Gln Ala Ala Arg
                20                  25                  30

Glu Leu Phe Leu Asp Trp Asp Thr
                35                  40
```

( 2 ) INFORMATION FOR SEQ ID NO:2:

( i ) SEQUENCE CHARACTERISTICS:
        ( A ) LENGTH: 32 amino acids
        ( B ) TYPE: amino acid
        ( C ) STRANDEDNESS: Not Relevant
        ( D ) TOPOLOGY: linear ( i i ) MOLECULE TYPE: protein ( v i ) ORIGINAL SOURCE:
        ( A ) ORGANISM: Brevibacterium lactofermentum
        ( B ) STRAIN: 2256 (ATCC 13869)

( x i ) SEQUENCE DESCRIPTION: SEQ ID NO:2:

Asn Lys Thr Asp Phe Ala Glu Ile Glu Leu Tyr Asp Val Leu Tyr Thr
1               5                   10                  15

Asp Ala Asp Ile Ser Gly Asp Ala Pro Leu Leu Ala Pro Ala Tyr Lys
            20                  25                  30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:3:

TTCATCGCTG CTGTCGGCAA CATCAACGAG                                                30

( 2 ) INFORMATION FOR SEQ ID NO:4:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: 2256 (ATCC 13869)

( x i ) SEQUENCE DESCRIPTION: SEQ ID NO:4:

AACAATGCAG ATCAGGCTGC ACGTGAGCTC TTCCTCGATT GGGACACC                            48

( 2 ) INFORMATION FOR SEQ ID NO:5:

( i ) SEQUENCE CHARACTERISTICS:
        ( A ) LENGTH: 2653 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: 2256 (ATCC 13869)

( i x ) FEATURE:
        ( A ) NAME/KEY: CDS
        ( B ) LOCATION: 912..2402

( x i ) SEQUENCE DESCRIPTION: SEQ ID NO:5:

ACTGGGAGGC TATCTCCATT GGGCGGTGCT GTCATCGTTG GCAGCTTTTC CATCCTGGAT               60

GGGGTTCTGG GCAGGACTGC CTTTGGCGGT CCTGTTAAAC GTCGCGGTTT GGTTGTACAC              120

CATCTATTCG ATGGCAACCA TGGATGAAGA TGATGCGCGG CTGCAAGGGG AAACAGCTCC              180

GTCATACTTT GAACGGATGC TGTGGGTGTG CAAAATTTCG TTGTGGGGCA TTGATTTTTG              240

GAAAAAGTAT CGCATCGCAT TAGCGATGTC TAAATCTTGG CTGAAACCAT ACATTTGCT               300

GTGTGCGAAC TGTATATCAG CTGATATTGC GCCTAAATTC CTGTGAATTA GCTGATTTAG              360

TACTTTTCGG AGGTGTCTAT TCTTACCAAA TTCGTCAAGT TGTGGGTAGA GTCACCTGAA              420

TATTAATTGC ACCGCACCGG GTGATATATG CTTATTTGCC TCAAGTAGTT CGAGGTTAAG              480

TGTATTTTAG GTGAACCAAA TTTCAGCTTC GGGTAGAAGA CTTTCGATGC GCTTCAGAGC              540

```
TTCTATTGGG AAATCTGACA CCACTTGATT AAATAGCCTA CCCCCGAATT GGGGAGATTG      600

GTCATTTTTT GCTGTGAAGG TAGTTTTGAT GCATATGACC TGCCGTTTAT AAAGAAATGT      660

AACGTGATCA GATCGATATA AGAACAGTT GTACTCAGGT TTGAAGGCAT CTCCGATTC       720

GCTGGCAAAT CTCATTGTCG GCTTACAGTT TTCTCAACGA CAGGCGTGCT AAGCTGCTAG      780

TTCAGGTGGC CTAGTGAGTG GCGTTTACTT GGATAAAAGT AATCCCATGT CGTGATCAGC     840

CATTTGGGT TGTTTCCATA GCAATCCAAA GGTTTCGTCT TTCGATACCT ATTCAAGGAG      900
```

```
CCTTCGCCTC T ATG TTT AAC AAC CGT ATC CGC ACT GCA GCT CTT GCT GGT      950
             Met Phe Asn Asn Arg Ile Arg Thr Ala Ala Leu Ala Gly
              1               5                   10

GCA ATC GCA ATC TCC ACC GCA GCT TCC GGC GTA GCT ATC CCA GCA TTC       998
Ala Ile Ala Ile Ser Thr Ala Ala Ser Gly Val Ala Ile Pro Ala Phe
     15              20                  25

GCT CAG GAG ACC AAC CCA ACC TTC AAC ATC ACC AAC GGC TTC AAC GAT      1046
Ala Gln Glu Thr Asn Pro Thr Phe Asn Ile Thr Asn Gly Phe Asn Asp
 30              35                  40                   45

GCT GAT GGA TCC ACC ATC CAG CCA GTT GAG CCA GTT AAC CAC ACC GAG      1094
Ala Asp Gly Ser Thr Ile Gln Pro Val Glu Pro Val Asn His Thr Glu
             50                  55                  60

GAA ACC CTC CGC GAC CTG ACT GAC TCC ACC GGC GCT TAC CTG GAA GAG      1142
Glu Thr Leu Arg Asp Leu Thr Asp Ser Thr Gly Ala Tyr Leu Glu Glu
             65                  70                  75

TTC CAG TAC GGC AAC GTT GAG GAA ATC GTT GAA GCA TAC CTG CAG GTT      1190
Phe Gln Tyr Gly Asn Val Glu Glu Ile Val Glu Ala Tyr Leu Gln Val
             80                  85                  90

CAG GCT TCC GCA GAC GGA TTC GAT CCT TCT GAG CAG GCT GCT TAC GAG      1238
Gln Ala Ser Ala Asp Gly Phe Asp Pro Ser Glu Gln Ala Ala Tyr Glu
         95              100                 105

GCT TTC GAG GCT GCT CGC GTT CGT GCA TCC CAG GAG CTC GCG GCT TCC      1286
Ala Phe Glu Ala Ala Arg Val Arg Ala Ser Gln Glu Leu Ala Ala Ser
110              115                 120                 125

GCT GAG ACC ATC ACT AAG ACC CGC GAG TCC GTT GCT TAC GCA CTC AAG      1334
Ala Glu Thr Ile Thr Lys Thr Arg Glu Ser Val Ala Tyr Ala Leu Lys
                 130                 135                 140

GCT GAC CGC GAA GCT ACC GCA GCT TTC GAG GCT TAC CTC AGC GCT CTT      1382
Ala Asp Arg Glu Ala Thr Ala Ala Phe Glu Ala Tyr Leu Ser Ala Leu
             145                 150                 155

CGT CAG GTT TCA GTC ATC AAC GAT CTG ATC GCT GAT GCT AAC GCC AAG      1430
Arg Gln Val Ser Val Ile Asn Asp Leu Ile Ala Asp Ala Asn Ala Lys
             160                 165                 170

AAC AAG ACT GAC TTT GCA GAG ATC GAG CTC TAC GAT GTC CTT TAC ACC      1478
Asn Lys Thr Asp Phe Ala Glu Ile Glu Leu Tyr Asp Val Leu Tyr Thr
    175                 180                 185

GAC GCG GAC ATC TCT GGC GAT GCT CCA CTT CTT GCT CCT GCA TAC AAG      1526
Asp Ala Asp Ile Ser Gly Asp Ala Pro Leu Leu Ala Pro Ala Tyr Lys
190                 195                 200                 205

GAG CTG AAG GAC CTT CAG GCT GAG GTT GAC GCA GAC TTC GAG TGG TTG      1574
Glu Leu Lys Asp Leu Gln Ala Glu Val Asp Ala Asp Phe Glu Trp Leu
                 210                 215                 220

GGC GAG TTC GCA ATT GAT AAC AAT GAA GAC AAC TAC GTC ATT CGT ACT      1622
Gly Glu Phe Ala Ile Asp Asn Asn Glu Asp Asn Tyr Val Ile Arg Thr
             225                 230                 235

CAC ATC CCT GCT GTA GAG GCA CTC AAG GCA GCG ATC GAT TCA CTG GTC      1670
His Ile Pro Ala Val Glu Ala Leu Lys Ala Ala Ile Asp Ser Leu Val
         240                 245                 250

GAC ACC GTT GAG CCA CTT CGT GCA GAC GCT ATC GCT AAG AAC ATC GAG      1718
Asp Thr Val Glu Pro Leu Arg Ala Asp Ala Ile Ala Lys Asn Ile Glu
    255                 260                 265
```

```
GCT CAG AAG TCT GAC GTT CTG GTT CCC CAG CTC TTC CTC GAG CGT GCA        1766
Ala Gln Lys Ser Asp Val Leu Val Pro Gln Leu Phe Leu Glu Arg Ala
270             275             280             285

ACT GCA CAG CGC GAC ACC CTG CGT GTT GTA GAG GCA ATC TTC TCT ACC        1814
Thr Ala Gln Arg Asp Thr Leu Arg Val Val Glu Ala Ile Phe Ser Thr
        290             295             300

TCT GCT CGT TAC GTT GAA CTC TAC GAG AAC GTC GAG AAC GTT AAC GTT        1862
Ser Ala Arg Tyr Val Glu Leu Tyr Glu Asn Val Glu Asn Val Asn Val
        305             310             315

GAG AAC AAG ACC CTT CGC CAG CAC TAC TCT TCC CTG ATC CCT AAC CTC        1910
Glu Asn Lys Thr Leu Arg Gln His Tyr Ser Ser Leu Ile Pro Asn Leu
        320             325             330

TTC ATC GCA GCG GTT GGC AAC ATC AAC GAG CTC AAC AAT GCA GAT CAG        1958
Phe Ile Ala Ala Val Gly Asn Ile Asn Glu Leu Asn Asn Ala Asp Gln
335             340             345

GCT GCA CGT GAG CTC TTC CTC GAT TGG GAC ACC GAC CTC ACC ACC AAC        2006
Ala Ala Arg Glu Leu Phe Leu Asp Trp Asp Thr Asp Leu Thr Thr Asn
350             355             360             365

GAT GAG GAC GAA GCT TAC TAC CAG GCT AAG CTC GAC TTC GCT ATC GAG        2054
Asp Glu Asp Glu Ala Tyr Tyr Gln Ala Lys Leu Asp Phe Ala Ile Glu
        370             375             380

ACC TAC GCA AAG ATC CTG ATC AAC GGT GAA GTT TGG CAG GAG CCA CTC        2102
Thr Tyr Ala Lys Ile Leu Ile Asn Gly Glu Val Trp Gln Glu Pro Leu
        385             390             395

GCT TAC GTC CAG AAC CTG GAT GCA GGC GCA CGT CAG GAA GCA GCT GAC        2150
Ala Tyr Val Gln Asn Leu Asp Ala Gly Ala Arg Gln Glu Ala Ala Asp
        400             405             410

CGC GAA GCA GAG CGC GCT GAC GCA GCA TAT TGC CGC GCT GAG CAG CTC        2198
Arg Glu Ala Glu Arg Ala Asp Ala Ala Tyr Cys Arg Ala Glu Gln Leu
        415             420             425

CGC ATC GCT CAG GAA GCA GCT GAC GCT CAG AAG GCT TTC GCT GAG GCT        2246
Arg Ile Ala Gln Glu Ala Ala Asp Ala Gln Lys Ala Phe Ala Glu Ala
430             435             440             445

CTG CTA ATG CCA GGC AAC AAC GAC AAC GGT GGC GAC AAC TCC TCC GAC        2294
Leu Leu Met Pro Gly Asn Asn Asp Asn Gly Gly Asp Asn Ser Ser Asp
        450             455             460

GAC AAG GGA ACC GGT TCT TCC GAC ATC GGA ACC TGG GGA CCT TTC GCA        2342
Asp Lys Gly Thr Gly Ser Ser Asp Ile Gly Thr Trp Gly Pro Phe Ala
        465             470             475

GCA ATT GCA GCT ATC ATC GCA GCA ATC GCA GCT ATC TTT CCA TTC CTC        2390
Ala Ile Ala Ala Ile Ile Ala Ala Ile Ala Ala Ile Phe Pro Phe Leu
        480             485             490

TCC GGT ATC GGT TAAGTTCTAA TTTCGAACCG AGATAGCTAA AAGTTAAACC           2442
Ser Gly Ile Gly
        495

ACCTCCTTTC CTTGGCCGGG AGGTGGTTTT TCCCTTGTTT AATTGCACTA AAAGAAAAGC     2502

CACCTCCTGC TTTAAAGGAG GTGGCTTTTC TTCGTCTACC TAGTTGAAAT AGAGGTGGGC     2562

GTCGATAAGC AAAAATCTTT TGCTTTTAAG GGAACGTGAT AATCGGCTTA ATGACCTCCC     2622

GCTGGCAGAA TCTGCAAAGG CATCATTGAT C                                    2653
```

( 2 ) INFORMATION FOR SEQ ID NO:6:

( i ) SEQUENCE CHARACTERISTICS:
        ( A ) LENGTH: 497 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Phe | Asn | Asn | Arg | Ile | Arg | Thr | Ala | Ala | Leu | Ala | Gly | Ala | Ile | Ala |
| 1 | | | | 5 | | | | | 10 | | | | | 15 | |
| Ile | Ser | Thr | Ala | Ala | Ser | Gly | Val | Ala | Ile | Pro | Ala | Phe | Ala | Gln | Glu |
| | | | 20 | | | | | 25 | | | | | 30 | | |
| Thr | Asn | Pro | Thr | Phe | Asn | Ile | Thr | Asn | Gly | Phe | Asn | Asp | Ala | Asp | Gly |
| | | 35 | | | | | 40 | | | | | 45 | | | |
| Ser | Thr | Ile | Gln | Pro | Val | Glu | Pro | Val | Asn | His | Thr | Glu | Glu | Thr | Leu |
| | 50 | | | | | 55 | | | | | 60 | | | | |
| Arg | Asp | Leu | Thr | Asp | Ser | Thr | Gly | Ala | Tyr | Leu | Glu | Glu | Phe | Gln | Tyr |
| 65 | | | | | 70 | | | | | 75 | | | | | 80 |
| Gly | Asn | Val | Glu | Glu | Ile | Val | Glu | Ala | Tyr | Leu | Gln | Val | Gln | Ala | Ser |
| | | | | 85 | | | | | 90 | | | | | 95 | |
| Ala | Asp | Gly | Phe | Asp | Pro | Ser | Glu | Gln | Ala | Ala | Tyr | Glu | Ala | Phe | Glu |
| | | | | 100 | | | | | 105 | | | | | 110 | |
| Ala | Ala | Arg | Val | Arg | Ala | Ser | Gln | Glu | Leu | Ala | Ala | Ser | Ala | Glu | Thr |
| | | | 115 | | | | | 120 | | | | | 125 | | |
| Ile | Thr | Lys | Thr | Arg | Glu | Ser | Val | Ala | Tyr | Ala | Leu | Lys | Ala | Asp | Arg |
| | | 130 | | | | | 135 | | | | | 140 | | | |
| Glu | Ala | Thr | Ala | Ala | Phe | Glu | Ala | Tyr | Leu | Ser | Ala | Leu | Arg | Gln | Val |
| 145 | | | | | 150 | | | | | 155 | | | | | 160 |
| Ser | Val | Ile | Asn | Asp | Leu | Ile | Ala | Asp | Ala | Asn | Ala | Lys | Asn | Lys | Thr |
| | | | | 165 | | | | | 170 | | | | | 175 | |
| Asp | Phe | Ala | Glu | Ile | Glu | Leu | Tyr | Asp | Val | Leu | Tyr | Thr | Asp | Ala | Asp |
| | | | 180 | | | | | 185 | | | | | 190 | | |
| Ile | Ser | Gly | Asp | Ala | Pro | Leu | Leu | Ala | Pro | Ala | Tyr | Lys | Glu | Leu | Lys |
| | | 195 | | | | | 200 | | | | | 205 | | | |
| Asp | Leu | Gln | Ala | Glu | Val | Asp | Ala | Asp | Phe | Glu | Trp | Leu | Gly | Glu | Phe |
| 210 | | | | | 215 | | | | | 220 | | | | | |
| Ala | Ile | Asp | Asn | Asn | Glu | Asp | Asn | Tyr | Val | Ile | Arg | Thr | His | Ile | Pro |
| 225 | | | | | 230 | | | | | 235 | | | | | 240 |
| Ala | Val | Glu | Ala | Leu | Lys | Ala | Ala | Ile | Asp | Ser | Leu | Val | Asp | Thr | Val |
| | | | | 245 | | | | | 250 | | | | | 255 | |
| Glu | Pro | Leu | Arg | Ala | Asp | Ala | Ile | Ala | Lys | Asn | Ile | Glu | Ala | Gln | Lys |
| | | | 260 | | | | | 265 | | | | | 270 | | |
| Ser | Asp | Val | Leu | Val | Pro | Gln | Leu | Phe | Leu | Glu | Arg | Ala | Thr | Ala | Gln |
| | | 275 | | | | | 280 | | | | | 285 | | | |
| Arg | Asp | Thr | Leu | Arg | Val | Val | Glu | Ala | Ile | Phe | Ser | Thr | Ser | Ala | Arg |
| | 290 | | | | | 295 | | | | | 300 | | | | |
| Tyr | Val | Glu | Leu | Tyr | Glu | Asn | Val | Glu | Asn | Val | Glu | Asn | Val | Glu | Asn | Lys |
| 305 | | | | | 310 | | | | | 315 | | | | | 320 |
| Thr | Leu | Arg | Gln | His | Tyr | Ser | Ser | Leu | Ile | Pro | Asn | Leu | Phe | Ile | Ala |
| | | | | 325 | | | | | 330 | | | | | 335 | |
| Ala | Val | Gly | Asn | Ile | Asn | Glu | Leu | Asn | Asn | Ala | Asp | Gln | Ala | Ala | Arg |
| | | | 340 | | | | | 345 | | | | | 350 | | |
| Glu | Leu | Phe | Leu | Asp | Trp | Asp | Thr | Asp | Leu | Thr | Thr | Asn | Asp | Glu | Asp |
| | | 355 | | | | | 360 | | | | | 365 | | | |
| Glu | Ala | Tyr | Tyr | Gln | Ala | Lys | Leu | Asp | Phe | Ala | Ile | Glu | Thr | Tyr | Ala |
| | 370 | | | | | 375 | | | | | 380 | | | | |
| Lys | Ile | Leu | Ile | Asn | Gly | Glu | Val | Trp | Gln | Glu | Pro | Leu | Ala | Tyr | Val |
| 385 | | | | | 390 | | | | | 395 | | | | | 400 |
| Gln | Asn | Leu | Asp | Ala | Gly | Ala | Arg | Gln | Glu | Ala | Ala | Asp | Arg | Glu | Ala |
| | | | | 405 | | | | | 410 | | | | | 415 | |
| Glu | Arg | Ala | Asp | Ala | Ala | Tyr | Cys | Arg | Ala | Glu | Gln | Leu | Arg | Ile | Ala |

|  | 420 |  |  |  | 425 |  |  |  | 430 |  |  |  |
|---|---|---|---|---|---|---|---|---|---|---|---|---|
| Gln | Glu | Ala | Ala | Asp | Ala | Gln | Lys | Ala | Phe | Ala | Glu | Ala | Leu | Leu | Met |
|  |  | 435 |  |  |  |  | 440 |  |  |  |  | 445 |  |  |  |

| Pro | Gly | Asn | Asn | Asp | Asn | Gly | Gly | Asp | Asn | Ser | Ser | Asp | Asp | Lys | Gly |
|---|---|---|---|---|---|---|---|---|---|---|---|---|---|---|---|
|  | 450 |  |  |  |  | 455 |  |  |  |  | 460 |  |  |  |  |

| Thr | Gly | Ser | Ser | Asp | Ile | Gly | Thr | Trp | Gly | Pro | Phe | Ala | Ala | Ile | Ala |
|---|---|---|---|---|---|---|---|---|---|---|---|---|---|---|---|
| 465 |  |  |  |  | 470 |  |  |  |  | 475 |  |  |  |  | 480 |

| Ala | Ile | Ile | Ala | Ala | Ile | Ala | Ala | Ile | Phe | Pro | Phe | Leu | Ser | Gly | Ile |
|---|---|---|---|---|---|---|---|---|---|---|---|---|---|---|---|
|  |  |  |  | 485 |  |  |  |  | 490 |  |  |  |  | 495 |  |

Gly ( 2 ) INFORMATION FOR SEQ ID NO:7:

( i ) SEQUENCE CHARACTERISTICS:
        ( A ) LENGTH: 2693 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: YSR ( x i ) SEQUENCE DESCRIPTION: SEQ ID NO:7:

```
ACTGGGAGGC TATCTCCATT GGGCGGTGCT GTCATCGTTG GCAGCTTTTC CATCCTGGAT      60
GGGGTTCTGG GCAGGACTGC CTTTGGCGGT CCTGTTAAAC GTCGCGGTTT GGTTGTACAC     120
CATCTATTCG ATGGCAACCA TGGATGAAGA TGATGCGCGG CTGCAAGGGG AAACAGCTCC     180
GTCATACTTT GAACGGATGC TGTGGGTGTG CAAAATTTCG TTGTGGGGCA TTGATTTTTG     240
GAAAAAGTAT CGCATCGCAT TAGCGATGTC TAAATCTTGG CTGAAACCAT TACATTTGCT     300
GTGTGCGAAC TGTATATCAG CTGATATTGC GCCTAAATTC CTGTGAATTA GCTGATTTAG     360
TACTTTTCGG AGGTGTCTAT TCTTACCAAA TTCGTCAAGT TGTGGGTAGA GTCACCTGAA     420
TATTAATTGC ACCGCACCGG GTGATATATG CTTATTTGCC TCAAGTAGTT CGAGGTTAAG     480
TGTATTTTAG GTGAACCAAA TTTCAGCTTC GGGTAGAAGA CTTTCGATGC GCTTCAGAGC     540
TTCTATTGGG AAATCTGACA CCACTTGATT AAATAGCCTA CCCCGAATT GGGGAGATTG      600
GTCATTTTTT GCTGTGAAGG TAGTTTTGAT GCATATGACC TGCCGTTTAT AAAGAAATGT     660
AACGTGATCA GATCGATATA AGAACAGTT GTACTCAGGT TTGAAGGCAT CTCCGATTC      720
GCTGGCAAAT CTCATTGTCG GCTTACAGTT TTCTCAACGA CAGGCGTGCT AAGCTGCTAG     780
TTCAGGTGGC CTAGTGAGTG GCGTTTACTT GGATAAAAGT AATCCCATGT CGTGATCAGC     840
CATTTGGGT TGTTTCCATA GCAATCCAAA GGTTTCGTCT TTCGATACCT ATTCAAGGAG      900
CCTTCGCCTC TATGTTTAAC AACCGTATCC GGCACTGCAG CTCTCGCATG GTGCAATCGC     960
AATCTCCACC GCAGCTTCCG GCGTAGCTAT CCCAGCATTC GCTCAGGAGA CCAACCCAAC    1020
CTTCAACATC AACCAACGGC TTCAACGATG CTGATGGATC CACCATCCAG CCAGTTGAGC    1080
CAGTTAACCA CACCGAGGAA ACCCTCCGCG ACCTGACTGA CTCCACCGGC GCTTACCTGG    1140
AAGAGTTCCA GTACGGCAAC GTTGAGGAAA TCGTTGAAGC ATACCTGCAG GTTCAGGCTT    1200
CCGCAGACGG ATTCCGGATC CTTCTGAGCA GGCTGCTTTA CGAGGCTTTC GAGGCTGCTC    1260
GCGTTCGTGC ATCCCAGGAG CTCGCGGCTT CCGCTGAGAC CATCACTAAG ACCCGCGAGT    1320
CCGTTGCTTA CGCACTCAAG GCTGACCGCG AAGCTACCGC AGCTTTCGAG CTTACCTCA     1380
GCGCTCTTCG TCAGGTTTCA GTCATCAACG ATCTGATCGC TGATGCTAAC GCCAAGAACA    1440
```

| | | | | | |
|---|---|---|---|---|---|
|AGACTGACTT|TGCAGAGATC|GAGCTCTACG|ATGTCCTTTA|CACCGACGCG|GACATCTCTG 1500|
|GCGATGCTCC|ACTTCTTGCT|CCTGCATACA|AGGAGCTGAA|GGACCTTCAG|GTGCATACAA 1560|
|GGAGCTGAAG|GACCTTCAGG|CTGAGGTTGA|CGCAGACTTC|GAGTGGTTGG|GCGAGTTCGC 1620|
|AATTGATAAC|AATGAAGACA|ACTACGTCAT|TCGTACTCAC|ATCCCTGCTG|TAGAGGCACT 1680|
|CAAGGCACGC|GATCGATTCA|CTGGTCGACA|CCGTTGAGCC|ACTTCGTGCA|GACGCTATCG 1740|
|CTAAGAACAT|CGAGGCTCAG|AAGTCTGACG|TTCTGGTTCC|CCAGCTCTTC|TCGAGCGTGC 1800|
|AACTGCACAG|CGCGACACCC|TGCGTGTTGT|AGAGGCAATC|TTCTCTACCT|CTGCTCGTTA 1860|
|CGTTGAACTC|TACGAGAACG|TCGAGAACGT|TAACGTTGAG|AACAAGACCC|TTCGCCAGCA 1920|
|CTACTCTTCC|CTGATCCCTA|ACCTCTTCAT|CGCAGCGGTT|GGCAACATCA|ACGAGCTCAA 1980|
|CAATGCAGAT|CAGGCTGCAC|GTGAGCTCTT|CCTCGATTGG|GACACCGACC|TCACCACCAA 2040|
|CGATGAGGAC|GAAGCTTACT|ACCAGGCTAA|GCTCGACTTC|GCTATCGAGA|CCTACGCAAA 2100|
|GATCCTGATC|AACGGTGAAG|TTTGGCAGGA|GCCACTCGCT|TACGTCCAGA|ACCTGGATGC 2160|
|AGGCGCACGT|CAGGAAGCAG|CTGACCGCGA|AGCAGAGCGC|GCAGTGACGC|AGCATATTGC 2220|
|CGCGCTGAGC|AGCTCCGCAT|CGCTCAGGAA|GCAGCTGACG|CTCAGAAGGC|TCTTCGCTGA 2280|
|GGCTCTGCTA|ATGCCAGGCA|ACAACGACAA|CGGTGGCGAC|AACTCCTCCG|ACGACAAGGG 2340|
|AACCGGTTCT|TCCGACATCG|GAACCTGGGG|ACCTTTCGCA|GCAATTGCAG|CTATCATCGC 2400|
|AGCAATCGCA|GCTATCTTTC|CCATTCCTCT|CCGGTATTCG|GTTAAGTTCT|AATTTCGAAC 2460|
|CGAGATAGCT|AAAAGTTAAA|CCACCTCCTT|TCCTTGGCCG|GGAGGTGGTT|TTTCCCTTGT 2520|
|TTAATTGCAC|TAAAAGAAAA|GCCACCTCCT|GCTTTAAAGG|AGGTGGCTTT|TCTTCGTCTA 2580|
|CCTAGTTGAA|ATAGAGGTGG|GCGTCGATAA|GCAAAAATCT|TTTGCTTTTA|AGGGAACGTG 2640|
|ATAATCGGCT|TAATGACCTC|CCGCTGGCAG|AATCTGCAAA|GGCATCATTG|ATC 2693|

DNA ENCODING NOVEL CELL SURFACE PROTEIN

This is a Division of application Ser. No. 08/295,670 filed on Sep. 8, 1994, now U.S. Pat. No. 5,547,864, which was filed as International Application No. PCT/JP94/00039 on Jan. 13, 1994.

TECHNICAL FIELD

The present invention concerns breeding of microorganisms useful for production of useful substances such as L-amino acids by fermentation processes and methods for producing useful substances such as L-amino acids by fermentation processes using the above-mentioned microorganisms. More specifically, it relates to a novel cell surface layer protein derived from *Brevibacterium lactofermentum*, a DNA segment containing a gene coding for the protein and an application use thereof.

BACKGROUND ART

Coryneform bacteria are microorganisms producing L-amino acids such as L-glutamic acid or L-lysin in a great amount and breeding for them has been conducted with an aim of improving the productivity of L-amino acids. Various studies have been made and reported so far for breeding of amino acid-producing bacteria using gene manipulation technology (Biotechnology letters, 2 (1980) 525–530, Appln. Environ. Microbiol., 144 (1979) 181–190, Abstruct of Lecture for the Meeting of the Society of Agricultural Chemistry of Japan (1981) 8). However, all of them have been directed to the improvement of the productivity of aimed amino acid per cell by utilizing genes in amino acid biosynthetic systems as materials and enhancing them and not directed to the improvement of the productivity by analyzing the function of a cell surface structure.

By the way, when an amino acid is produced by a fermentation process, ion exchange chromatography has usually been conducted in the course of purifying a produced amino acid but, if bacterial cells remain in a fermentation medium, an ion exchange resin column is clogged when the fermentation medium is passed through the column and, accordingly, a step of removing the bacterial cells from the fermentation medium is necessary. The step is usually conducted by centrifugation, filtration or the like and it will be extremely useful industrially if such cell separating operation can be saved or simplified.

It has been known that microbial cells are precipitated in the medium due to aggregation or the like after cultivation depending on the kind of microorganisms and separation of the cells from a culture medium is extremely easy for such microorganisms. However, no Coryneform bacteria used in amino acid production, having such a property have yet been reported and a method of providing microbial cells with aggregating or precipitating property has not yet been known as well.

The published pamphlet of WO 93/03158 discloses a novel cell surface layer protein similar to a K-protein of the present invention, but this protein is clearly distinguished from the K-protein. Further, this publication discloses a protein expression-secretion system utilizing a signal peptides of the cell surface-layer protein but it has not yet been known that such protein contributes to incorporation of nutrients of Coryneform bacteria and aggregating nature of bacterial cells.

Further, while Coryneform bacteria have been used industrially as L-amino acid-producing bacteria, it has been found recently that the bacteria are highly secretory and there has been an attempt of utilizing them for the production of different protein already put to practical use for Bacilli. The above-mentioned international publication WO 93/03158 also discloses a technology of such kind.

The subject to be dissolved by the present invention is to obtain a novel cell surface layer protein that contributes to the incorporation of nutrients of Coryneform bacteria and a gene thereof, and obtain a transformant obtained by amplification of the gene in the cell of Coryneform bacteria. The present invention also has a subject of using Coryneform bacteria having an activity to produce useful substances such as L-amino acids as a host for the transformant and improving the process for producing the useful substances such as L-amino acids by fermentation processes using the above-mentioned host bacteria, as well as obtaining Coryneform bacteria having a aggregating property, which is deficient in the novel cell surface layer protein, to simplify a process of amino acid production.

DISCLOSURE OF THE INVENTION

As a result of an earnest study, the present inventors have succeeded in obtaining a novel cell surface layer protein and a gene thereof which contribute to incorporation of a nutrient of bacteria and have accomplished the present invention.

Specifically, the present invention provides a novel cell surface layer protean derived from *Brevibacterium lactofermentum* having following two sequences, (1) Thr—Leu—Arg—Gln—His—Tyr—Ser—Ser—Leu—Ile—Pro—Asn—Leu—Phe—Ile—Ala—Ala—Val—Gly—Asn—Ile—Asn—Glu—Leu—Asn—Asn—Ala—Asp—Gln—Ala—Ala—Arg—Glu—Leu—Phe—Leu—Asp—Trp—Asp—Thr (SEQ ID NO:1) and
(2) Asn—Lys—Thr—Asp—Phe—Ala—Glu—Ile—Glu—Leu—Tyr—Asp—Val—Leu—Tyr—Thr—Asp—Ala—Asp—Ile—Ser—Gly—Asp—Ala—Pro—Leu—Leu—Ala—Pro—Ala—Tyr—Lys (SEQ ID NO:2)

in the molecule, and having a molecular weight of about 63,000 dalton, a DNA fragment containing a gene coding for the protein, a recombinant DNA obtained by ligating the DNA fragment with a vector capable of autonomous replication in a cell of Coryneform bacteria, a transformant obtained by introducing and amplifying the DNA fragment in the cell of Coryneform bacteria and a method for producing useful substances such as L-amino acid by fermentation processes which comprises culturing the transformant having an activity to produce useful substance such as L-amino acid in a culture medium, forming and accumulating the useful substance in the culture medium and collecting the useful substance from the culture medium.

The present invention provides Coryneform bacteria having a cell aggregating property and being deficient in the cell surface layer protein described above or a protein substantially identical with the above-mentioned protein being present in the cell surface of Coryneform bacteria.

The present invention also provides Coryneform bacteria having a cell aggregating property and being deficient in the cell surface layer protein, in which a gene coding for the cell surface layer protein or a gene coding for a protein which is substantially identical with the above-mentioned protein and is present in the cell surface of Coryneform bacteria is destroyed by homologous recombination of a DNA fragment containing at Least a portion of a gene coding for the cell surface Layer protein with a DNA sequence on a chromosome which is identical or homologous with the DNA fragment.

The present invention further provides a process for producing a useful substance, comprising:

cultivating Coryneform bacteria having an activity to produce useful substance such as L-amino acid;

forming and accumulating the useful substance in a culture medium and:

collecting the useful substance from the culture medium, wherein the Coryneform bacteria is deficient in the above-mentioned novel cell surface layer protein and has a cell aggregating property, and further comprising a step of standing still the culture medium after the completion of cultivation thereby precipitating the cells of Coryneform bacteria.

The Coryneform bacteria referred to in the present invention are, as described later, a group of microorganisms which are bacilliform, aerobic, gram positive, non-acid-fast and asporogenous (as defined in Bargeys Manual of Determinative Bacteriology, 8th edition, 599p (1974)). Specific microorganisms belonging to such Coryneform bacteria may also be referred to hereinafter simply as "Coryneform bacteria". Further, the Coryneform bacteria being deficient in the cell surface layer protein according to the present invention and the Coryneform bacteria in which a gene coding for the cell surface layer protein is destroyed may sometimes be referred to collectively as "K-protein-deficient strain".

1. Novel cell surface layer protein, its gene, transformant thereof and a process of production of L-amino acid The novel cell surface layer protein in the present invention is obtained as described below. Cells of *Brevibacterium lactofermentum*, for example, strain 2256 (ATCC 13869) are disrupted, for example, using a supersonicator (OHTAKE 5202PZT), then the cell lysate is centrifuged under a condition stronger than the condition of 3,000×g for 5 min at 4° C., preferably, 12,000×g for 1 min at 4° C. to recover supernatant. Then, the supernatant is centrifuged under a condition stronger than the condition of 100,000×g for 20 min at 4° C., preferably, 100,000×g for 30 min at 4° C., and precipitates are recovered as a cell surface layer fraction. The protein present in a great amount around a molecular weight of 63,000 in this fraction is a novel cell surface layer protein according to the present invention, that is, the K-protein.

The K-protein is purified as described below. The prepared cell surface layer fraction contains both of cytoplasmic membrane and cell wall. Then, they are separated by solubilizing the cytoplasmic membrane using a surface active agent. Since the extent of solubilization differs depending, for example, on the kind and concentration of the surface active agent, time and temperature of the solubilization process and concentration of additional glycerol and/or NaCl, the present invention can be completed only when the optimum conditions for the purification are found. Determination for the optimum conditions has been established for the first time according to the present invention. That is, 3.0 μg of an cell surface layer fraction is added to 1 ml of a buffer solution (50 mM potassium phosphate, pH 8.0, 0.1 mM dithiothreitol) containing 1.25% (w/v) SDS , kept at 4° to 90° C., preferably, at 37° C. for more than 30 min, preferably, for one hour, then applied with centrifugation under a condition stronger than the condition of 145, 000×g for 20 min, preferably, 145,000×g for 30 min and precipitates are recovered. The precipitates are suspended in 50 mM potassium phosphate at pH 8.0 containing 0.1% SDS such that the suspension contains 0.01–10 μg protein/μl, preferably, 0.2 μg protein/μl, and then solubilized by boiling for about 3 min.

The molecular weight of the K-protein is estimated from the mobility in SDS-polyacrylamide gel electrophoresis (Gel Electrophoresis of Proteins, IRL Press (1981) B. D. Hammes, et al). The molecular weight of the K-protein is estimated as about 63,000.

The amino acid sequence of the K-protein is determined as described below. The purified K-protein is suspended in 50 mM Tris-HCl, pH 7.3 containing 0.1% SDS such that the suspension contains of 10 μg protein/ml–2 mg protein/ml, preferably, 200 μg protein/ml and the suspesion is boiled for about 5 min to solubilize the K-protein. After allowing the solution to cool, the solution is added with endoprotenase Lys-C (manufactured by Boeringer Manhaim Co.) such that the ratio of the protein fraction insoluble in a surface active agent and Lys-C is about 10:1–200:1, preferably, 50:1 (wt/wt) and incubated at 37° C. for more than 30 min, preferably, at 37° C. for 3 hours.

The K-protein partialy digested with Lys-C is fractionated by reverse phase chromatography. Commercially available columns may be properly selected for the chromatography, for example, Senshu Pac VP-318-1251 4.6ø×250 mm can be used. Elution is carried out by using a gradient solution such as $CH_3CN$-0.1% TFA. The flow rate may be at 1 ml/min. Among thus obtained fractions, a fraction of higher peptide content is used to determine the amino acid sequence. The method of determination is according to a known method (P. Edman, Arch. Biochem. 22 475 (1949)), for example, by using a Gas Phase Sequencer 470-A manufactured by Applied Biosystems Co. and in accordance with the supplier's manual.

The K-protein has following two sequences in the molecule:

(1)Thr—Leu—Arg—Gln—His—Tyr—Ser—Ser—Leu—Ile—Pro—Asn—Leu—Phe—Ile—Ala—Ala—Val—Gly—Asn—Ile—Asn—Glu—Leu—Asn—Asn—Ala—Asp—Gln—Ala—Ala—Arg—Glu—Leu—Phe—Leu—Asp—Trp—Asp—Thr (sequence table, SEQ ID NO:1) and
(2)Asn—Lys—Thr—Asp—Phe—Ala—Glu—Ile—Glu—Leu—Tyr—Asp—Val—Leu—Tyr—Thr—Asp—Ala—Asp—Ile—Ser—Gly—Asp—Ala—Pro—Leu—Leu—Ala—Pro—Ala—Tyr—Lys (sequence table, SEQ ID NO:2).

K-protein gene is isolated as follows. Chromosomal DNA is at first extracted from *Brevibacterium lactofermentum*, for example, strain 2256 (ATCC 13869) (a method for example described by H. Saito and K. Miura, in Biochem. Biophys. Acta 72, 610 (1963) can be used), and digested with an appropriate restriction enzyme. A wide variety of restriction enzymes can be used if the extent of digestion of the chromosomal DNA is controled by regulation of the reaction condition, for example reaction time.

The DNA fragment and a vector DNA capable of replicating in the cell of a microorganism belonging to the genus Escherichia are ligated to form a recombinant DNA, and then the Escherichia bacteria, for example, *Escherichia coli* strain JM109 is transformed with the recombinant DNA to prepare a genomic DNA library. The k-protein gene can be isolated from the library by colony hybridization using a synthetic DNA having a nucleotide sequence deduced from a known amino acid sequence as a probe.

Specifically, chromosomal DNA of *Brevibacterium lactofermentum*, strain 2256 (ATCC 13869) is partially digested with a restriction enzyme, for example, Sau3AI at a temperature higher than 30° C., preferably, 37° C. at an enzyme concentration of 1 to 10 unit/ml for various times (1 min to 2 hours), to obtain mixtures of various size of chromosomal DNA fragments. The vector DNA capable of replicationg in the cells of Escherichia bacteria is completely cleaved with a restriction enzyme causing an identical terminal base sequence with that of the restriction enzyme Sau3AI used for digesting the chromosomal DNA, for example, BamHI, at a temperature higher than 30° C. and an enzyme concentration of 1 to 100 unit/ml for more than one hour, preferably, for 1 to 3 hours to obtain cleaved and linearized DNA. Then, the mixture containing the DNA fragment including the K-protein gene derived from *Brevibacterium lactofermentum* strain 2256 (ATCC 13869) obtained as described above and the linearized vector DNA are mixed and ligated using DNA ligase, preferably, T4 DNA ligase at a temperature of 4° to 16° C., an enzyme concentration of 1 to 100 units, for more than one hour, preferably, 6 to 24 hours to obtain a recombinant DNA.

As the vector DNA that can be used in the present invention, a plasmid vector DNA is preferred and there can be mentioned, for example, pUC19, pUC18, pBR322, pHSG299, pHSG399 and RSF1010. In addition, a phage DNA vector can also be used. For efficiently expressing the K-protein gene, a promotor operating in microorganisms such as lac, trp, PL may also be used. The recombinant DNA referred to herein may include a recombinant DNA obtained by integrating the K-protein gene into chromosome by a method of using transposon (Berg. D. E. and Berg. C. M. Bio/Technol., 1 417 (1983)), MU phage (Japanese Patent Laid-Open Publication 90-109985) or by homologous recombination (Experiments in Molecular Genetics, Cold Spring Harbor Lab. (1972)).

A gene library is prepared by transforming, for example, *Escherichia coli* K-12, preferably, JM109 with the above-mentioned recombinant DNA. A method of preparing the gene library is detailed in Molecular Cloning second edition (Cold Spring Harbor Press (1989) Maniatis, et al.). Transformation can be performed by the method of D. M. Morrison (Methods in Enzymology 68, 326, 1979) or a method of enhancing DNA permeability by treating recipient cells with calcium chloride <Mandel, M. and Higa, A., J. Mol. Biol., 53, 159 (1970)).

Successively, a recombinant DNA containing a DNA fragment that includes the K-protein gene is isolated from the gene library by a colony hybridization method. The colony hybridization can be perfomed in accordance with the method as described in Molecular Cloning second edition (Cold Spring harbor Press (1989) Maniatis, et al.).

As a DNA probe used in the colony hybridization, a synthetic DNA having a base sequence deduced from the amino acid sequence of the purified K-protein is used. For example, a 30 mer oligonucleotide having a sequence of 5'-TTCATCGCTGCTGTCGGCAACATCAACGAG-3' (SEQ ID No: 3)

synthesized by using a DNA Synthesizer manufactured by Applied Biosystems Co. can be mentioned preferably. Upon determination of the sequence, presence of a plurality of codons corresponding to a kind of amino acid residue results in a remarkable hindrance. In view of the above, the sequence is determined by selecting a region in which the degree of degeneracy of the codons corresponding to each amino acid is low or by referring to the codon usage of the genus Brevibacterium. Oligonucleotide can be synthesized in accordance with a customary manner by using a DNA Synthesizer Model 380B manufactured by Applied Biosystems Co. and using a phosphoamidide method (refer to Tetrahedron Letters, 22, 1859 (1981)).

Alternatively, the K-protein gene can also be obtained by amplifying the K-protein genes from the chromosomal DNA obtained, for example, by a method of H. Saito and K. Miura Biochem. Biophys. Acta. 72, 619 (1963) by PCR (polymerase chain reaction: White, T. J. et al: Trends Genet, 5, 185 (1989). DNA primers used for PCR are complementary to sequences of both 3' termini of double-stranded DNA including a whole or a partial region of the K-protein gene.

In a case of amplifying only a partial region of the K-protein gene, it is necessary to screen the DNA fragment including the whole K-protein gene from the gene library by using the above-mentioned DNA fragment as a probe. In a case of amplifying the whole gene, DNA fragments including the K-protein gene Can be recovered by separation of PCR reaction mixture by agarose gel electrophoresis and then cutting out a band containing the desired DNA fragment from an agarose gel.

As the DNA primer, a synthetic DNA having a base sequence deduced from the purified K-protein amino acid sequence is used. Upon determination of the sequence, presence of a plurality of codons corresponding to a kind of amino acid residue results in a remarkable hindrance. In view of the above, the sequence is determined by selecting a region in which the degree of degeneracy of the codons corresponding to each amino acid is low or by referring to the codon usage of the genus Brevibacterium. The DNA can be synthesized in accordance with a customary method by using a DNA Synthesizer Model 380B manufactured by Applied by Biosystem Co. and using the phosphoamidide method. The PCR reaction can be conducted by using DNA Thermal Cycler Model PJ2000 manufactured by Takara Shuzo Co., using a Taq DNA polymerase and in accordance with a method designated by the supplier.

The DNA fragment containing the whole K-protein gene or a partial region of the K-protein gene amplified by the PCR reaction is ligated to a vector DNA capable of replicating in cells of bacteria belonging to the genus Escherichia to form a recombinant DNA. Then the recombinant DNA is introduced into the cell of bacteria belonging to the genus Escherichia. The vector DNA and the transforming method used herein are identical as those described previously. In a case of amplifying only a partial region of the K-protein gene, a DNA fragment containing the whole K-protein gene can be isolated from the gene library by using the above-mentioned DNA fragment as a probe. As the isolation method, the colony hybridization method described previously may be used.

Whether the isolated DNA fragment containing the K-protein gene actually contains the K-protein gene or not is confirmed by nucleotide sequencing of the DNA fragment using the synthetic DNA used for colony hybridization or PCR as a primer and by confirming if the determined nucleotide sequence codes for the above-mentioned amino acid sequence. The nucleotide sequence can be determined by a dideoxy method (Molecular Cloning second edition (Cold Spring Harbor Press (1989), Maniatis et al)).

Whether the K-protein is the novel cell surface layer protein contributing to the incorporation of nutrients of Coryneform bacteria or not can be confirmed by preparing K-protein-deficient strain and measuring the activity of the K-protein-deficient strain to incorporate ammonium ions. Then, it is confirmed that the numerical value shows remarkable reduction as compared with the ammonium ion incorporating activity of a K-protein sufficient strain.

Then, explanation will be made to a recombinant DNA obtained by ligating the DNA fragment containing the K-protein gene with a vector capable of autonomous replication in the cells of Coryneform bacteria, a transformant of Coryneform bacteria obtained by introduction and amplification of the DNA fragment in the cell and a process for producing L-amino acid by a fermentation process which comprises cultivating the above-mentioned transformant having L-amino acid productivity, forming and accumulating L-amino acid in a culture medium and collecting the L-amino acid from the culture medium.

The Coryneform bacteria referred to in the present invention, for example, microorganisms belonging to Brevibacterium or Corynebacterium are a group of microorganisms defined in Bargeys Manual of Determinative Bacteriology (8th edition, p 599, (1974)), which are bacilliform, aerobic, gram positive, non-acid-fast and asporogenous. Among The microorganisms of Brevibacterium or Corynebacterium, L-glutamic acid producing bacteria belonging to the genus Brevibacterium or the genus Corynebacterium described below can be used in the present invention.

As examples of wild type strains of glutamic acid producing bacteria belonging to the genus Brevibacterium or the genus Corynebacterium, there can be mentioned the followings.

| | |
|---|---|
| *Brevibacterium dibaricatum* | ATCC 14020 |
| *Brevibacterium saccharoriticum* | ATCC 14066 |
| *Brevibacterium immariofiltn* | ATCC 14068 |
| *Brevibacterium lactofermentum* | ATCC 13869 |
| *Brevibacterium roseum* | ATCC 13825 |
| *Brevibacterium flabum* | ATCC 13826 |
| *Brevibacterium thiogenetallis* | ATCC 19240 |
| *Brevibacterium acetoacidfilum* | ATCC 13870 |
| *Brevibacterium acetoglutamicum* | ATCC 15806 |
| *Brevibacterium cainae* | ATCC 15991 |
| *Corynebacterium glutamicum* | ATCC 13032, 13060 |
| *Corynebacterium lilyum* | ATCC 15990 |
| *Corynebacterium meracecola* | ATCC 17965 |
| *Microbacterium ammoniafilum* | ATCC 15354 |

Any vector DNA that can replicate in the bacterial cells of Brevibacterium or Corynebacterium can be used in the present invention. There can be specifically exemplified the followings.

| | |
|---|---|
| (1) pAM 330 | refer to Japanese Patent Laid-Open Publication 83-67699 |
| (2) pHM 1519 | refer to Japanese Patent Laid-Open Publication 83-77395 |
| (3) pAJ 655 | refer to Japanese Patent Laid-open Publication 83-192900 |
| (4) pAJ 611 | refer to Japanese Patent Laid-open Publication 83-192900 |
| (5) pAJ 1844 | refer to Japanese Patent Laid-open Publication 83-192900 |
| (6) pCG 1 | refer to Japanese Patent Laid-Open Publication 82-134500 |
| (7) pCG 2 | refer to Japanese Patent Laid-Open Publication 83-35197 |
| (8) pCG 4 | refer to Japanese Patent Laid-Open Publication 82-183799 |
| (9) pCG 11 | refer to Japanese Patent Laid-Open Publication 82-183799 |

The vector DNA is cleaved with a restriction enzyme that cleaves the vector DNA at a unique site, or by partially cleaved with a restriction enzyme that cleaves the DNA at a plurality of its recognition sites.

The vector DNA is cleaved with the restriction enzyme used for cleavage of the DNA fragment that codes for the K-protein gene and ligated with the DNA fragment. If the vector DNA is cleaved with a restriction enzyme which forms different termini from that of the DNA fragment that codes for the K-protein gene, oligonucleotide linkers having base sequence complementary to termini of the linearized vector are ligated to both termini of the DNA fragment, and then the linker-tailed DNA fragment is ligated with the vector DNA.

Resulting recombinant DNA in which the vector DNA and the DNA fragment that codes for the K-protein gene are ligated can be introduced into recipients belonging to the genus Brevibacterium or the genus Corynebacterium, by a method of enhancing the DNA permeability by treating the recipient cells with calcium chloride as reported for *Escherichia coli* K-12 (Mandel, M. and Higa, A., J. Mol., Biol., 53 159 (1970), or a method of introducing DNA into a exponential stage of cells such that cells can incorporate the DNA (so-called competent cell) as reported for *Bacillus subtilis* (Duncan, C. H., Wilson, G. A. and Young, F. E., Gene, 1 153 (1977)). Alternatively, the recombinant DNA can also be introduced into bacterial cells by converting the cells into protoplasts or spheroplasts capable of readily incorporating the recombinant DNA as known for *Bacillus subtilis*, Actinomycetes and yeasts (Chang, S. and Choen, S. N., Molec. Gen., Genet., 168 111 (1979); Bibb, M. J., Ward, J. M. and Hopwood, O. A., Nature, 274, 398 (1978); Hinnen, A., Hicks, J. B. and Fink, G. R. Proc. Natl. Acad. Sci. U.S.A., 75, 1929 (1978)).

In the protoplast method, a sufficiently high frequency of transformation can be obtained also by a method used for *Bacillus subtilis* described above, and a method of incorporating the DNA into the protoplast of Corynebacterium or Brevibacterium under the presence of polyethylene glycol or polyvinyl alcohol and divalent metal ions disclosed by Japanese Patent Laid-Open Publication 82-183799 can of course be utilized. Similar effect can be obtained also by a method of promoting the incorporation of the DNA, for example, by addition of carboxymethyl cellulose, dextran, ficoll or Bulronic F68 (manufactured by Selba Co.) instead of polyethylene glycol or polyvinyl alcohol.

Further, the recombinant DNA can be introduced into the recipient bacteria belonging to the genus Brevibacterium or the genus Corynebacterium also by an electric pulse method (also called electroporation) (Sugimoto, et al., Japanese Patent Laid-Open Publication 90-207791).

L-amino acid producing transformant obtained by the method described above, which harbors the recombinant DNA containing the DNA fragment that codes for the K-protein is cultivated and an aimed L-amino acid is produced and accumulated in a culture medium, which is then collected.

The culture medium for L-amino acid production used herein is a usual culture medium containing a carbon source, nitrogen source, inorganic ions and if necessary, other organic ingredients.

As the carbon source, saccharides such as glucose, lactose, galactose, fructose or hydrolyzates of starch. alcohols such as glycerol or sorbitol, and organic acid such as fumaric acid, citric acid and succinic acid can be used.

As the nitrogen source, inorganic ammonium salts such as ammonium sulfate, ammonium chloride and ammonium phosphate, organic nitrogen such as hydrolyzates of soybean, gaseous ammonia and ammonium hydroxide can be used.

As the organic micro-nutrients, culture medium is desirable to be added with required substances such as vitamin B1 or yeast extract in appropriate amount. In addition, a small amount of potassium phosphate, magnesium sulfate, iron ions, manganese ions, etc. is added if necessary.

Cultivation is preferably carried out under an aerobic condition for 16 to 72 hours, while controlling cultivation temperature at 30° C. to 45° C. and pH at 5 to 7 during cultivation. Inorganic or organic acidic or alkaline substance and, further, gaseous ammonia etc. can be used for pH adjustment. L-amino acid can be collected from the fermentation liquid by a combination of usual ion exchange resin method, precipitation method and other known method.

By the way, Coryneform bacteria are microorganisms producing L-amino acids in a great amount and have been utilized generally for the production of L-amino acids by the fermentation process. In addition, high secreting property of the Coryneform bacteria have also been utilized for the production of various materials.

Since it is considered that the K-protein is present in the cell surface layer and contributes to the incorporation of nutrients into cytoplasm, if a transformant of Coryneform bacteria obtained by the introduction and replication of DNA fragments containing the K-protein gene in the cell has a useful substance productivity, it is considered that a process for producing useful substance by the fermentation process which comprises cultivating the transformant in a culture medium, forming and accumulating the useful substance in the culture medium and collecting the useful substance from the culture medium also can be improved.

The main part of the process for producing the useful substance, which comprises cultivating the transformant in the culture medium, forming and accumulating the useful substance in the culture medium and collecting the useful substance from the culture medium, is identical with the process for producing amino acids described above.

The useful substance referred to herein includes nucleic acids as raw material for seasonings. The Coryneform bacteria producing nucleic acids include, for example, *Corynebacterium equi* AJ 11347 as disclosed in Japanese Patent Publication 82-22558.

On the other hand, the useful substance means foreign proteins. Namely, there can be mentioned physiologically active substances such as human interferon, human interleukin or human hormone, enzyme or antibody. Methods of producing foreign proteins by using microorganisms have been known mainly for bacteria of Escherichia or Bacillus, and a similar technique has also been developed for Coryneform bacteria. The technique basically comprises preparing a recombinant DNA by ligating a vector capable of autonomous replication in the cells of Coryneform bacteria with a promotor that can operate in the cells of Coryneform bacteria and a DNA fragment that codes for the foreign protein, introducing the recombinant DNA into the Coryneform bacteria and producing the protein through expression of the DNA that codes for the protein on the recombinant DNA. The technology is disclosed, for example, in Japanese Patent Laid-Open Publication 87-151184 or Japanese Patent Laid-Open Publication 87-244382.

(2) K-protein-deficient strain and a process for producing L-amino acid utilizing them As described above, it has been confirmed that the K-protein found for the first time according to the present invention contributes to the incorporation of nutrients of the Coryneform bacteria and it is further disclosed by the present invention that the Coryneform bacteria also contribute to aggregating property of bacterial cells and Coryneform bacteria which is deficient in the K-protein exhibit aggregating nature.

The K-protein-deficient strain are obtained by causing such a mutation as not substantially producing the K-protein to the K-protein gene, for example of *Brevibacterium lactofermentum*. Alternatively, a spontaneous mutant strain having such a mutation as not substantially producing the K-protein may be selected from the natural world.

Further, the K-protein-deficient strain can also be obtained by destroying the K-protein gene by homologous recombination between a DNA fragment containing at least a portion of a gene that codes for the K-protein and the K-protein gene on the chromosome.

Further, it is anticipated that even Coryneform bacteria other than *Brevibacterium lactofermentum* have a protein identical with or substantially identical with the K-protein (hereinafter referred to as a "K-protein-like protein") in cell surface layer. For instance, the published pumphlet of WO 93/03158 describes a novel cell surface layer protein which is similar to but can be distinguished clearly from the K-protein of the present invention.

It is expected that such a K-protein-like protein also contributes to the incorporation of nutrients or to the aggregating property of bacterial cells and the Coryneform bacteria being deficient in the K-protein-like protein also have a aggregating property.

The Coryneform bacteria being deficient in the K-protein-like protein can be obtained, in the same manner as the K-protein-deficient strain, by causing such mutation as not substantially producing the K-protein-like protein to the K-protein-like protein gene. Further, a spontaneous mutant strain having such mutation as not substantially producing the K-protein-like protein may be selected from the natural world. Further, Coryneform bacteria being deficient in the K-protein-like protein can also be obtained by destroying the gene coding for the K-protein-like protein by homologous recombination between a DNA fragment containing at least a portion of a K-protein gene and a gene coding for K-protein-like protein on the chromosome which is homologous with the DNA fragment.

Description will now be made to a method of obtaining the K-protein-deficient strain. In the following descriptions, if the K-protein is replaced with the K-protein-like protein, the strain being deficient in the K-protein-like protein can be obtained also in the same manner.

Mutation not substantially producing the K-protein can be caused to the K-protein gene by applying a usual method of causing artificial mutation to microorganisms such as UV-ray irradiation or by a treatment with a mutagenic agent such as N-methyl-N'-nitro-N-nitrosoguanidine (NTG).

As a method of selecting the K-protein-deficient strain from the Coryneform bacteria subjected to mutagenization, there can be mentioned, for example, a method using an anti-K-protein antibody, for instance, a Western blotting method. More specifically, colonies of mutagenized Coryneform bacteria are formed on a membrane such as a nylon membrane placed on an agar medium plate to fix the cellular protein on the membrane. In this case, a replica plate is prepared on a separate agar medium plate such that 1:1 correspondence is obtained with the colonies on the membrane. Then, when the membrane is immersed successively into solutions containing an anti-K-protein antibody, an enzyme-labelled second antibody against an immunoglobulin fraction of immunized animal used for preparation of the anti-K-protein antibody, and dyes that develops color through an enzymatic reaction caused by the labeling enzyme, respectively, and then incubated, a color is developed at a position to which the cell protein of the K-protein sufficient bacteria is fixed. Accordingly, the K-protein deficient bacteria can be selected by identifying the colony not causing the color development of the dye and isolating the colony from the replica plate corresponding to this colony. It is preferred that SDS-polyacrylamide gel electrophoresis is carried out for proteins of the cell surface layer fraction of thus selected K-protein-deficient strain to confirm that K-protein is not substantially expressed.

The anti-K-protein antibody is obtained by immunizing an animal such as mouse by using the K-protein prepared from the cell surface layer fraction of *Brevibacterium lactofermentum* as shown in (1) above, in the same manner as a usual preparation method for immunization and collecting blood. It is also possible to use an anti-K-protein monochronal antibody obtained by fusing spleen cell of an animal immunized by the K-protein and culture cell having a continuous growing activity such as a mouse myeloma cell to prepare hybridoma cell and cultivating the resulting hybrodoma cells.

The enzyme-labelled second antibody is obtained by forming a covalent bond between an enzyme such as β-galactosidase or horseradish peroxidase and an anti-immunogloblin antibody against an immunoglobulin fraction of an immunized animal used for the preparation of the anti-K-protein antibody. Enzyme-labeled antibodies agnainst immunoglobulin of various kinds of animals are commercially available and usable.

Another method of selecting K-protein-deficient strain from mutagenized Coryneform bacteria will be explained. A cell surface layer fraction is prepared by the method as described in (1) above for each of cells put to single colony isolation and obtained cell surface layer fraction is subjected to SDS-polyacrylamide gel electrophoresis. A strain for which no K-protein band is detected near the molecular weight of about 63,000 is the K-protein-deficient strain. Although the method is extremely time-consuming, it is desirable to adopt it for the secondary screening step since it can reliably select the K-protein-deficient strain.

By the same method as described above, a mutant strain having a mutation not substantially producing the K-protein can be selected from the natural world.

Then, explanation will be made to a method of obtaining the K-protein-deficient strain or K-protein-like protein-deficient strain by gene disruption. A DNA containing a DNA fragment that contains a portion of the K-protein gene is introduced into the cell of Coryneform bacteria, and homologous recombination is caused between the DNA fragment containing a portion of the K-protein gene and a DNA sequence on a chromosome which is identical or homologous with the DNA fragment, thereby enabling to interrupt the K-protein gene or the K-protein-like protein gene on the chromosomal DNA to deplete the K-protein or K-protein-like protein. A schematic view for the mechanism of the gene disruption is shown in FIG. 1.

More specifically, a DNA fragment containing a portion of the K-protein gene is ligated with a vector plasmid DNA, to prepare a plasmid for gene disruption. The plasmid for gene disruption is introduced into Coryneform bacteria such as Brevibacterium lactofermentum to obtain a transformant by a method of enhancing the DNA permeability by treating recipient cells with calcium chloride as reported for Escherichia K-12 (Mandel, M. and Higa, A., J. Mol., Biol., 53, 159 (1970), a method of introducing DNA into growing stage of cells such that cells can incorporate DNA as reported for Bacillus subtilis (so-called competent cell) (Duncan, C. H., Wilson, G. A. and Young, F. E., Gene, 1, 153 (1977)), a method of converting the DNA recipient into protoplast or spheroplast capable of easily incorporating DNA and introducing the recombinant plasmid into the DNA recipient as known for Bacillus subtilis, Actinomycetes and yeasts (Chang, S. and Choen, S. N., Molec. Gen., Genet., 168, 111 (1979), Bibb, M. J., Ward, J. M. and Hopwood, O. A., Nature, 274, 398 (1978); Hinnen, A. Hicks, J. B. and Fink, G. R. Proc. Natl. Acad. Sci. U.S.A., 75, 1929 (1978)), or a electric pulse method (Sugimoto, et al., Japanese Patent Laid-Open Publication 90-207791) in the same manner as in (1) described above.

For a vector plasmid used for the preparation of the plasmid for gene disruption, it is preferred to use a vector having a temperature sensitive replication origin, for example, pHSC4 (Sugimoto, et al., French Patent Laid-Open Publication No. 2667875/1992) and the resulting transformant is cultivated at a replication inhibitive temperature. This can prevent the plasmid from autonomous replication outside the chromosome in the cell and make the transformant in which the plasmid is incorporated into the chromosome DNA to be able to grow preferentially. Further, for facilitating the selection of the transformant, it is desirable to use such a vector plasmid as possessing a marker gene, for example, a drug resistant gene.

When the Coryneform bacteria to which the plasmid for gene distruption is introduced is cultivated in a culture medium containing drug corresponding to the marker gene, preferably, at replication-inhibitory-temperature, a transformant in which the plasmid is integrated into the chromosome only can grow. In such a transformant cell, the plasmid for gene destruction is integrated into the K-protein gene on the chromosome by the homologous recombination between the DNA fragment containing a portion of the K-protein gene possessed in the plasmid for gene destruction and the K-protein gene or the K-protein-like protein gene on the chromosome and, as a result, the chromosomal K-protein gene is probably disrupted. Whether thus obtained transformant is deficient in the K-protein or not can be confirmed by subjecting the cell surface layer fraction of the transformant to polyacrylamide gel electrophoresis. Further, it can also be confirmed by the required aggregating nature of the transformant cells.

As the Coryneform bacteria which is to be mutagenized for obtaining the K-protein-deficient strain or to be disrupted with the K-protein gene, there can be mentioned microorganisms of Brevibacterium or Corynebacterium as stated in (1) above.

Then, description will be made to a process for producing L-amino acid, comprising: cultivating Coryneform bacteria having an activity to produce L-amino acid, forming and accumulating L-amino acid in the culture medium and collecting the L-amino acid from the culture medium, wherein the Coryneform bacteria is deficient in the K-protein or K-protein-like protein, and further comprising a step of standing still the culture medium after the completion of cultivation and therby precipitating the cells of Coryneform bacteria.

Coryneform bacteria having an activity to produce the L-amino acid and being deficient the K-protein or K-protin-like protein are cultivated and an aimed L-amino acid is formed and accumulated in a culture medium. The culture medium used for the production of the L-amino acid is a usual culture medium containing a carbon source, a nitrogen source, inorganic ions and, if necessary, other organic ingredients.

As the carbon source, there can be used, for example, saccharides such as beat molasses, cane molasses, glucose, sucrose, lactose, galactose, fructose and hydrolyzates of starch, alcohols such as glycerol and sorbitol, and organic acids such as fumaric acid, citric acid and succinic acid.

As the nitrogen source, there can be used, for example, inorganic ammonium salts such as ammonium sulfate, ammonium chloride, ammonium phosphate, organic nitrogen such as hydrolyzates of soybean, gaseous ammonia and ammonia hydroxide.

As the organic micro-nutrient source, culture medium is desirable to added with an appropriate amount of required substance such as vitamin B1 or yeast extract. In addition, a small amount of potassium phosphate, magnesium sulfate, iron ions and manganese ions is added to culture medium as required.

Cultivation is preferably carried out under an aerobic condition for 16 to 72 hours while controlling the cultivation temperature at 30° C. to 45° C. and pH value at 5 to 7 during cultivation. For pH control, organic or inorganic acidic or alkaline substance and further gaseous ammonia may be used.

Since the culture medium composition and cultivation condition may give effects on the aggregating property of bacterial cells, conditions suitable to the obtained K-protein-deficient strain may be properly selected.

Then, after completion of the cultivation, the culture medium is allowed to stand and aggregated bacterial cells are precipitated to be separated from the cultivation supernatants. The cultivation supernatant and the bacterial cells can be separated by recovering the supernatants such that the precipitated bacterial cells are not intruded. Further, cell separation process may be carried out by means of ordinary centrifugal separation or filtration and the separation process is facilitated since the bacterial cells are aggregated.

After the separation of the bacterial cells, the L-amino acid can be collected from the fermentation medium by a combination of customary ion exchange chromatography, precipitation method and other known method. A basic amino acid such as L-lysin is usually purified by a cationic exchange chromatography after adjusting the pH value of the fermentation solution to about 4. Since the K-protein-deficient strain according to the present invention further increases the aggregating property at a pH value of about 4, if the cell precipitating step is carried out after pH adjustment, precipitation can be completed in a shorter period of time thereby enabling to separate bacterial cells more efficiently. Furthermore, the cultivation supernatants separated from the bacterial cells can be passed as they are through the ion exchange resin column.

The present invention shows that the K-protein contributes to the aggregating property of the cells, and this concept is applicable also to a cell removing step at the downstream in the fermentation industry other than production of L-amino acids, to a cell recycle type bioreactor and, further, to the improvement of the precipitation of active sludge bacteria, even in the fermentation industry other than that of L-amino acid.

For instance, when the Coryneform bacteria which has an activity to produce useful substance is deficient in the K-protein or K-protein-like protein and has cell aggregating property, this enables to improve the process for producing a useful substance by a fermentation process which comprises cultivating the bacteria in a culture medium, forming and accumulating the useful substance in the culture medium and collecting the useful substance from the culture medium. This is because the cell separating operation is essential also in these production processes.

That is, the cell separating operation is facilitated also in the same manner as the amino acid production process as described above in a process for producing a useful substance by a fermentation process comprising cultivating Coryneform bacteria having an activity to produce useful substance, forming and accumulating the useful substance in a culture medium and collecting the useful substance from the culture medium, wherein the Coryneform bacteria is deficient the K-protein or K-protein-like protein and has a cell aggregating property, and further comprising a step of standing still the culture medium after the completion of the cultivation thereby precipitating cells of the Coryneform bacteria.

The useful substance referred to herein includes a nucleic acid as a raw material for seasonings. The Coryneform bacteria producing the nucleic acid includes, for example, *Corynebacterium equi* AJ 11347 as disclosed in Japanese Patent Publication 82-22558.

Further, the useful substance also includes foreign proteins. That is, there can be mentioned physiologically active substances such as human interferon or human interleukin, enzyme or antibody. Methods of producing foreign proteins using microorganisms have been known mainly for bacteria belonging to the genus Escherichia or the genus Bacillus and similar technology has been developed also for Coryneform bacteria. These techniques basically comprises ligating a vector capable of autonomous replication in the cell of Coryneform bacteria with a promotor that can operate in the cell of the Coryneform bacteria and DNA coding for the foreign protein to form a recombinant DNA, introducing the recombinant DNA into the Coryneform bacteria and producing the protein through the expression of DNA coding for the protein on the recombinant DNA. This technique is disclosed for example in Japanese Patent Laid-Open Publication 87-151184.

○ . . . K-protein-sufficient strain (AEC$^r$ 2256)

● . . . K-protein-sufficient strain (AEC$^r$ 2256), CCCP (carbonylcyanide m-chlorophenyl hydrazine) added □ . . . K-protein-deficient strain (AJ 12760)

■ . . . K-protein-deficient strain (AJ 12760), CCCP added

Figure 3:
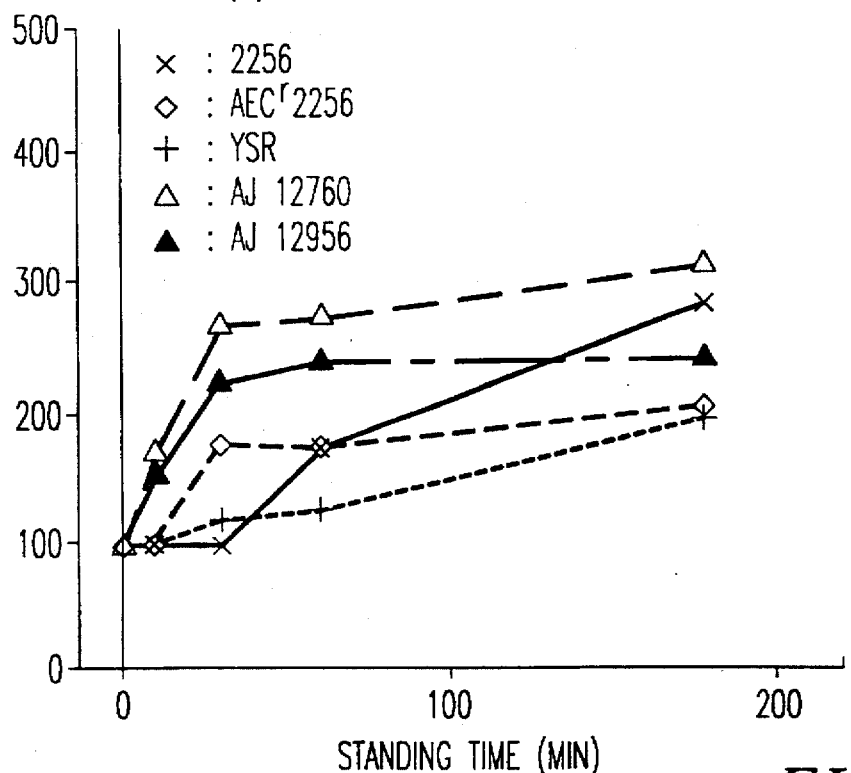

FIG. 3: diagram showing the precipitation degree of K-protein-deficient strain and K-protein-sufficient strain (Carbon source: glucose, culture medium after completion of cultivation adjusted to pH 4.0).

× . . . 2256 strain (ATCC 13869)

+ . . . YSR strain

◇ . . . AEC$^r$ 2256 strain

△ . . . AJ 12760

▲ . . . AJ 12956

The symbols shown above are also used for FIGS. 4 to 6.

Figure 4:
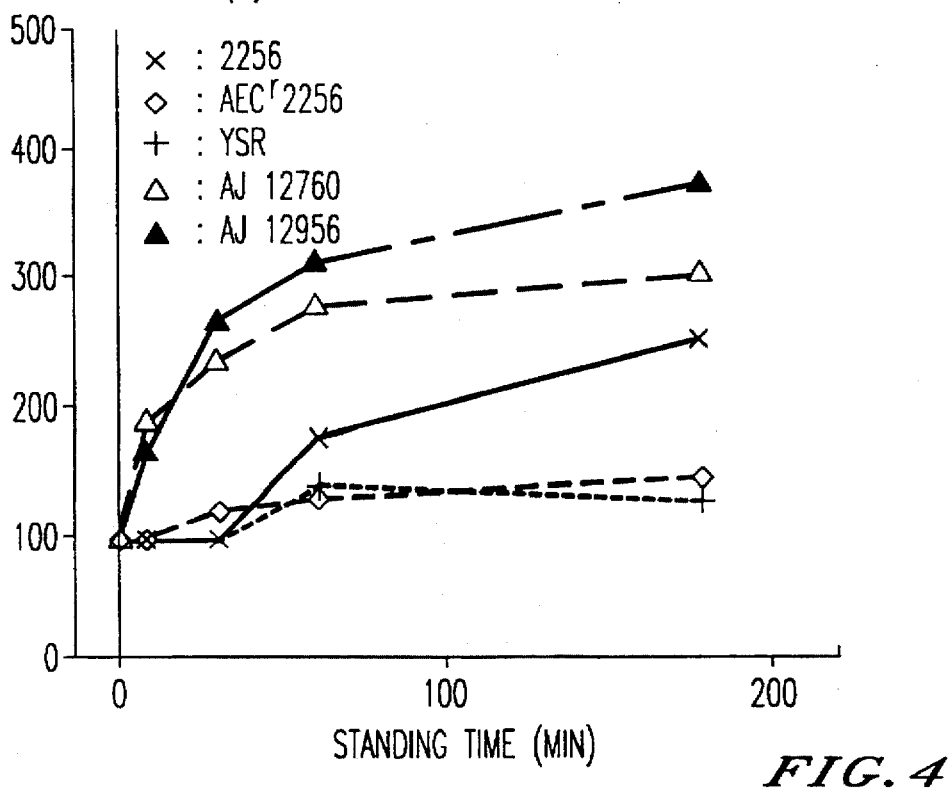

FIG. 4: diagram showing the precipitation degree of K-protein-deficient strain and K-protein-sufficient strain (Carbon source: sucrose, culture medium after completion of cultivation adjusted to pH 4.0).

Figure 5:
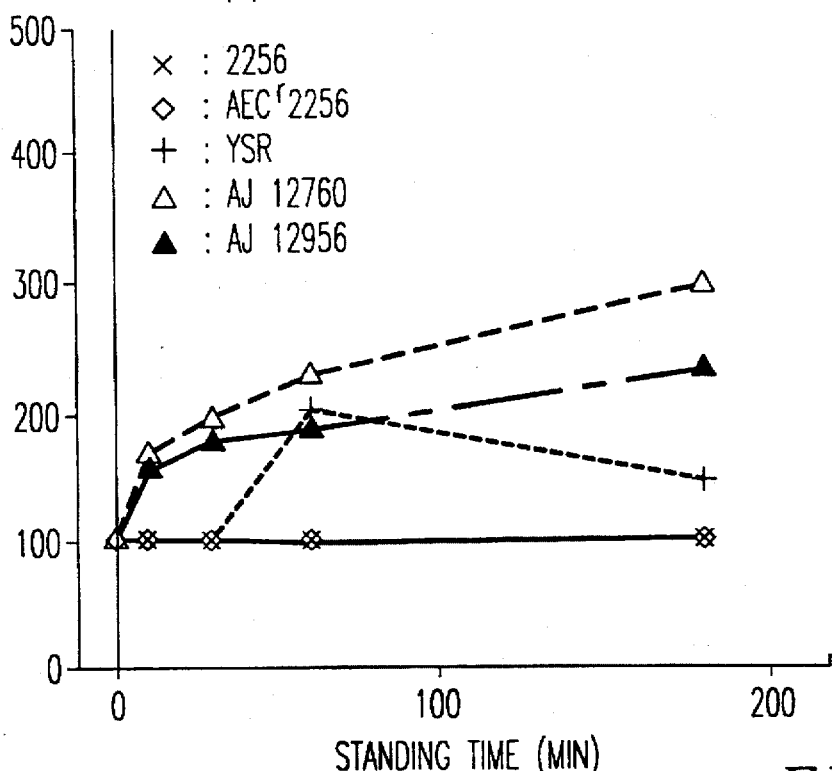

FIG. 5: diagram showing the precipitation degree of K-protein-deficient strain and K-protein-sufficient strain (Carbon source: glucose, culture medium after the completion of cultivation not adjusted for pH).

Figure 6:
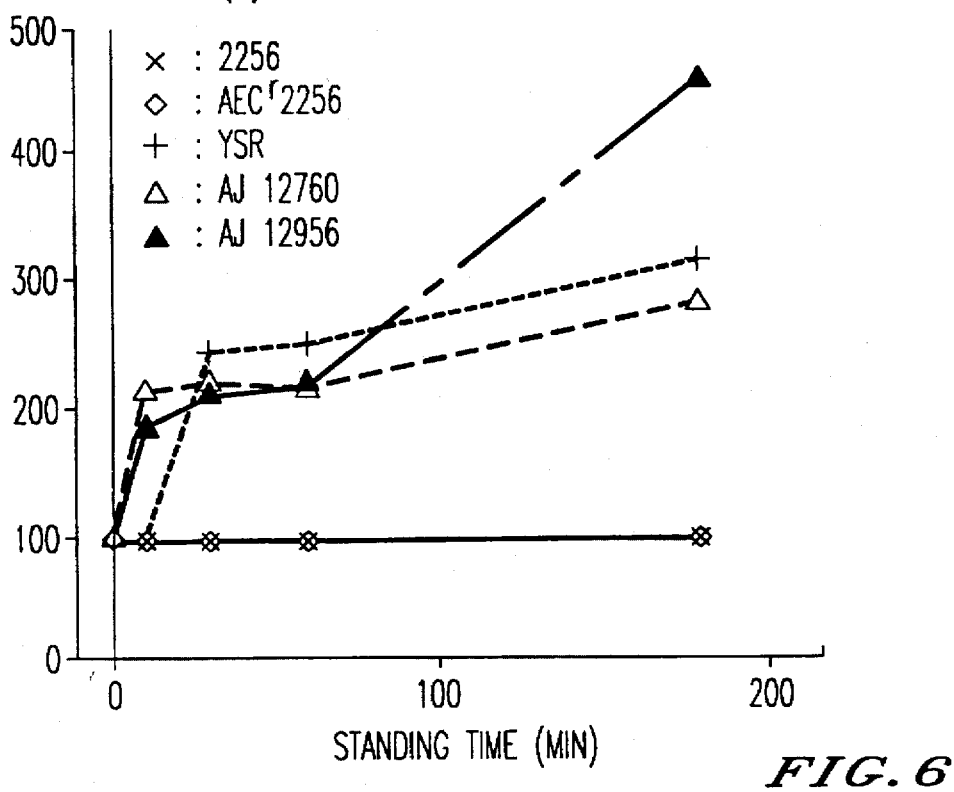

FIG. 6: diagram showing the precipitation degree of K-protein-deficient strain and K-protein-sufficient strain (Carbon source: sucrose, culture medium after the completion of cultivation not adjusted for pH).

BEST MODE FOR PRACTICING THE INVENTION

The present invention will now be described more concretely by way of examples.

EXAMPLE 1

Novel cell surface layer protein K-protein (1) Finding of novel cell surface layer protein

*Brevibacterium lactofermentum* ATCC 13869 was put to shaking cultivation over night at 30° C. in a CM2G culture medium (yeast extract 10 g, bacto tryprone 10 g, glucose 5 g, NaCl 5 g; filled up with water to 1 liter) and cells were collected from 1 ml of a culture both. After washing with a buffer solution A (50 mM potassium phosphate, pH 8.0, 10 mM magnesium sulfate), the cells were suspended in 1 ml of a buffer solution A, frozen and melted, and cells were broken by a supersonicator (OHTAKE 5202PZT) while keeping at 0° C. Then, the cell lyzate was centrifuged at 12,000×g for 1 min at 4° C. and supernatant was recovered. Obtained supernatant was re-centrifuged at 100,000×g for 30 min at 4° C. and precipitates were recovered as cell surface layer fractions. Among the fractions. a portion corresponding to 5×10⁹ cells was subjected to SDS-polyacrylamide gel electrophoresis. As a result, a protein band present in a great amount was found near the molecular weight of about 63,000 and this protein was named as K-protein.

The present inventors expected that the cell surface layer protein has a function to contribute to the incorporation of nutrients from the outside of the bacterial cell and proceeded the following experiments.

For the K-protein solution put to restricted digestion by the using Lys-C, a portion corresponding to 500 pmoles of K-protein was fractionated by reversed phase chromatography. A column used was Senshu Pac VP-318-1251 4.6ø×250 mm. Elution was performed with $CH_3CN$ gradient (24% $CH_3CN$, 0.1% TFA-66% $CH_3CN$, 0.1% TFA) at a flow rate of 1 ml/min. Among the fractions of eluent, amino acid sequence was determined for two fractions of high peptide content (fractions eluted by 55.7–57.0% $CH_3CN$ and 59.3–60.5% $CH_3CN$) using a Gas Phase Sequencer 470-A manufactured by Applied Biosystems Co. The amino acid sequence was determined by the method in accordance with the supplier's manual of Applied Biosystems Co. As a result, it has been found that the K-protein has following two sequences, in the molecule, that is, (1)Thr—Leu—Arg—Gln—His—Tyr—Ser—Ser—Leu—Ile—Pro—Asn—Leu—Phe—
Ile—Ala—Ala—Val—Gly—Asn—Ile—Asn—Glu—Leu—Asn—Asn—Ala—Asp—Gln—
Ala—Ala—Arg—Glu—Leu—Phe—Leu—Asp—Trp—Asp—Thr   (SEQ ID No: 1), and (2)Asn—Lys—Thr—Asp—Phe—Ala—Glu—Ile—Glu—Leu—Tyr—Asp—Val—Leu—
Tyr—Thr—Asp—Ala—Asp—Ile—Ser—Gly—Asp—Ala—Pro—Leu—Leu—Ala—Pro—
Ala—Tyr—Lys   (SEQ ID No: 2).

(2) Purification of K-protein

At first, a cell surface layer fraction was prepared by the method as described previously in (1). The cell surface layer fraction contained both cytoplasmic membranes and cell walls. Then, it was attempted to separate them by solubilizing the cytoplasmic membranes using a surface active agent. As a result of detailed studies for the kind and the concentration of the surface active agent, the time and the temperature for solubilization, the effect of adding glycerol and the effect of adding NaCl, the K-protein could be purified by the method to be described below. Three µg of a cell surface layer fraction of the protein (quantification is performed by the BC protein assay kit manufactured by Bio Rad Co.) was suspended into 1 ml of a buffer solution containing 1.25% (w/v) SDS (50 mM potassium phosphate, pH 8, 0.1 mM dithiothreitol) and the suspension was kept at 37° C. for one hour. Then the suspension was centrifuged at 145,000×g for 30 min and recovering precipitates. The precipitate was recovered by suspending in 50 mM potassium phosphate at pH 8.0, containing 0.1% SDS such that 0.2 µg protein/µl was contained, and boiling for 3 min. Fifteen µg of the protein as the surface active agent-insoluble fraction was subjected to SDS-polyacrylamide gel electrophoresis and it was confirmed that this is a homogeneous protein having a molecular weight of 63,000.

(3) Property of K-protein (3-1) Molecular weight

The molecular weight of the K-protein was estimated to about 63,000 based on the mobility in SDS-polyacrylamide gel electrophoresis.

(3-2) Determination of partial amino acid sequence

The K-protein purified by the method as described in (2) above was suspended in 50 mM Tris-HCl , pH 7.3, 0.1% SDS so as to give a concentration of 200 µg protein/ml and solubilized by boiling for 5 min. After allowing to cool, endoprotenase Lys-C was added to the solution such that the ratio of the protein as the surface active agent insoluble fraction and the Lys-C was 50:1 (wt/wt), and incubated at 37° C. for 3 hours.

EXAMPLE 2

Isolation of K-protein gene (1) Preparation of gene library

Chromosomal DNA was prepared from *Brevibacterium lactofermentum* 2256 (ATCC 13869) by a method of Saito and Miura (Biochem. Biophys. Acta., 8278 (1963) 619–629). Two units of Sau3AI was added to about 50 µg of the choromosomal DNA and partially digested by keeping a temperature at 37° C. for 40 min. Reaction mixture were centrifuged on sucrose density gradient (10%–40%) at 120, 000×g for 26 hours to fractionate the DNA fragments.

Fractions about from 1,500 to 6,000 bps were recovered (1.5 ml volume), which were dialyzed at 4° C. to a TE buffer (10 mM Tris-HCl, 1 mM EDTA, pH 8.0). The Seamless Cellulose Tubing Size 8/32 manufactured by Sanko Junyaku Co. was used as a dialyzing tube. Dialysis was applied for 4 hours to 2 liter of buffer and, conducted for further 2 hours after exchanging the buffer.

After dialysis, the chromosomal DNA fraction of 1,500–6,000 bps was extracted with 2-butanol in accordance with a method of Maniatis, et al.(Molecular Cloning second edition, Cold Spring Harbor Press (1989) Maniatis, et al), and then the DNA fragments were ligated to vector pSTV28 which was previously cleaved with BamHI (manufactured by Takara Shuzo Co.) by using T4DNA ligase (manufactured by Takara Shuzo Co.). *Escherichia coli* JM109 (manufactured by Takara Shuzo Co.) was transformed by the obtained ligation mixture in accordance with the supplier's manual of Takara Shuzo Co. to prepare a gene library consisting of about 5,000 clones. It is considered that a host harboring a vector in which the K-protein gene fragment is cloned becomes fetal if the K-protein gene is expressed at a high rate, therefore, a low copy vector pSTV28 was used.

(2) Cloning of K-protein gene

Based on the amino acid sequence in Example 1 (3-2), 30 mer oligonucleotide having a sequence of 5'-TTCATCGCTGCTGTCGGCAACATCAACGAG-3' (SEQ ID No:3) was synthesized by using a DNA synthesizer manufactured by Applied Biosysystems Co., as a probe used for colony hybridization. Upon determination of the sequence, presence of a plurality of codons corresponding to a kind of amino acid residue results in a significant hindrance and it is essential how to cope with this. In the present invention, it is possible to prepare an excellent probe by considering the two points described below and this is a large factor of the success. The two points are: (1) it was possible to select an amino acid region in which the degree of degeneracy of the codons corresponding to each amino acid is low since an amino acid sequence of a relatively long region can be determined and (2) although there was no definite knowledge regarding the frequency of codon usage of Brevibacterium, knowledge of Tsuchiya, et al. upon cloning lipase (Japanese Patent Laid-Open Publication 92-271780) was referred to.

A colony hybridizing with the probe was obtained from thus prepared gene library by colony hybridization. A HYBOND-N™ (nylon membrane) (manufactured by Amersham Co.) membrane was used for making a replica of the colony, hybridization was performed at 50° C. for 40 hours and then the filter was washed for four times under the condition at 40° C. for one hour. Secondary screening was performed for thus obtained hybridization-positive colonies by colony hybridization. Using the oligonucleotide described above as a probe and the HYBOND-N™ (nylon membrane) (manufactured by Amersham Co.) as the membrane for preparing a replica, hybridization was performed at 50° C. for 24 hours, and washing was applied for three times at 40° C. for one hour and twice at 50° C. for one hour. Twelve clones were selected in the secondary screening. Plasmid DNA were recovered by the alkali-SDS method from these 12 colonies which were positive in this secondary screening. From a result of examining cleavage patterns of these plasmids by digestion with Eco RI and HindIII (both manufactured by Takara Shuzo Co.), it was confirmed that each of the plasmids had a inserted DNA fragment at BamHI site of pSTV28.

Thus obtained DNA fragment was blotted on the HYBOND-N™ (nylon membrane) membrane using Vacu-Gene (manufactured by Pharmacia LKB Biotechnology Co.) in accordance with a supplier's manual thereof and Southern hybridization was performed using the oligonucleotide probe described above. Hybridization was performed under condition of at 50° C. for 26 hours and washing was applied once at 40° C. for one hour and once at 50° C. for one hour. As a result, it has been found that 6 out of 12 clones which were positive in the secondary screening are hybridized with the probe and the 6 clones could be calssified into three types based on a restriction enzyme cleaving pattern.

The nucleotide sequences for thus obtained three types of inserted DNA fragments were determined by a dideoxy method using the oligonucleotide described above as the primer, and it was found one type of the inserted DNA fragment contained a sequence of 5'-AACAATGCAGATCAGGCTGCACGTGAGCTCTTCC TCGATTGGGACACC-3, (SEQ ID NO:4). This sequence codes for the amino acid sequence which locates on the carboxy terminal side from a potion used for determination of the sequence of the probe in the amino acid sequence determined previously, that is, Asn-Asn-Ala-Asp-Gln-Ala-Ala-Arg-Glu-Leu-Phe-Leu-AsP-TrP-Asp-Thr (corresponding to amino acid Nos. 25–40 in SEQ ID No:1,) and, from this, it was confirmed that the DNA fragment contains at least a portion of the desired gene.

Then, the nucleotide sequence was determined for the entire length of the inserted DNA fragment by the dideoxy method. The determined base sequence is shown in the sequence table, SEQ ID No:5. It was found that the fragment coded for the K-protein. The amino acid sequence of the K-protein deduced from the nucleotide sequence is also described in the sequence table, SEQ ID No:5.

EXAMPLE 3

Preparation of K-protein-deficient strain
(1) Preparation of K-protein-deficient strains Using Brevibacterium lactofermentum 2256 strain(ATCC 13869) as a parent strain, mutation treatment with N-methyl-N'-nitro-N-nitrosoguanidine (NTG) was applied for whole cells. Cells of 2256 strain were cultivated in 2×TY medium (1.6% Bacto-trypton, 1% Yeast extract, 0.5% NaCl) and the cells were collected when optical absorption of the medium at 660 nm reached about 0.3. After washing the cells with a TM buffer solution of the composition shown in Table 1, they were suspended in an NTG solution (NTG dissolved in TM buffer solution at 0.2 mg/ml), and incubated at 37° C. for 0–90 min.

The NTG-treated cells were washed with the TM buffer solution and 2×TY medium and then cultivated in the 2×TY medium overnight to fix mutation.

TABLE 1

| Ingredient | Concentration |
|---|---|
| Tris | 50 mM |
| Maleic acid | 50 mM |
| (NH$_4$)$_2$SO$_4$ | 1 g/L |
| MgSO$_4$.7H$_2$O | 0.1 g/L |
| Ca(NO$_3$)$_2$ | 5 mg/L |
| FeSO$_4$.7H$_2$O | 0.25 mg/L |

Adjusted to pH 6.0 with NaOH

Single colony isolation was performed for cells mutagenized with NTG as described above and about 1,000 colonies were isolated. Each of the clones forming these colonies was examined whether K-protein is depleted or not. Cell surface layer fraction was prepared for each of the clones by the method as described in Example 1 (1) and a SDS-polyacrylamide gel electrophoresis experiment was performed using thus prepared fraction as the specimen. In this way, a strain in which fraction a band of K-protein was not detected around the molecular weight of 63,000, namely, the K-protein-deficient strain could be obtained. This strain was named as Brevibacterium lactofermentum YSR.

The chromosomal DNA of thus obtained YSR strain was examined whether the cause that the strain was deficient in the K-protein was derived from the gene or not. That is, the K-protein gene was cloned from the YSR strain to analyze the structure in the same manner as in Example 1.

A chromosomal DNA was prepared from the YSR strain by the method of Saito-Miura (Biochem. Biophys. Acta., 8278 (1963) 619–629). About 50 µg of the DNA was added with two units of Sau3AI and partially digested by incubation at the temperature at 37° C. for 40 min. Then the digested DNA was fractionated by centrifugation (120,000× g, 26 hours) on sucrose density gradient (10% to 40%).

Fractions corresponding to about 1,500–6,000 bps were collected (1.5 ml volume), and dialyzed to a TE buffer (10 mM Tris/HCl, 1 mM EDTA, pH 8.0) at 4° C. Seamless Cellulose Tubing Size 8/32 manufactured by Sanko Junyaku Co. was used as a dializing tube. Dialysis was applied to a 2 liter buffer for 4 hours and then applied for further 2 hours after replacing the buffer.

Thus obtained fraction of chromosomal DNA of 1,500–6,000 bps was extracted with 2-butanol according to the method of Maniatis, et al. (Molecular Cloning second edition, Cold Spring Harbor Press (1989) Maniatis, et al) and was ligated with vector pUC18 previously cleaved with BamHI (manufactured by Takara Shuzo Co.) using T4DNA ligase (manufactured by Takara Shuzo Co.). Then *Escherichia coli* JM109 (manufactured by Takara Shuzo Co.) was transformed with the ligation mixture according to the supplier's manual of Takara Shuzo Co. to prepare a gene library.

From the resulting gene library, clone possessing the K-protein gene was screened by colony hybridization using a synthetic DNA having a sequence of 5'-TTCATCGCTGCTGTCGGCAACATCAACGAG-3' obtained (SEQ ID NO:3) in Example 2 (2) as the probe. HYBOND-N™ (nylon membrane) (manufactured by Amersham Co.) membrane was used as a replica of the colony, hybridization was conducted at 50° C. for 40 hours and washing was applied for four times under a condition at 40° C. for one hour. Secondary screening was performed for hibridization-positive coronies by colony hybridization. Using the DNA described above as the probe and HYBOND-N™ (nylon membrane) (manufactured by Amersham Co.) as the membrane for preparing replica, hybridization was performed at 50° C. for 24 hours and washing was applied for three times at 40° C. for one hour and twice at 50° C. for one hour.

Plasmid DNAs were recovered by the alkali-SDS method from these colonies which were positive in this secondary screening. The inserted DNA fragment of the clone to be expected to contain the whole region of the K-protein gene by restriction enzyme clevage patterns was determined with nucleotide sequence by the dideoxy method. From the result, it has been proved that the K-protein gene isolated from the YSR strain had a sequence shown in the sequence table, SEQ ID No:7. When the sequence was compared with the sequence table, SEQ ID No:5, it has been found that the K-protein gene of YSR has the mutation shown below. The nucleotide numbers in Table 2 correspond to the base numbers in SEQ ID No:7.

TABLE 2

| nucleotide No. | Type of Mutation |
| --- | --- |
| 932 | G insertion |
| 945 | T → C mutation |
| 948 | A insertion |
| 1031 | A insertion |
| 1215–1216 | CG insertion |
| 1238 | T insertion |
| 1551–1579 | 29 base insertion |
| 1688 | C insertion |
| between 1789 and 1790 | C deletion |
| 2203–2204 | AG insertion |
| 2274 | C insertion |
| 2422 | C insertion |
| 2438 | T insertion |

It has been found that the K-protein gene on the chromosome of the YSR strain caused frame shift by deletion and insertions of the nucleotides as described above and, as a result, the YSR strain no more expressed the K-protein. The plasmid containing the mutant K-protein gene fragment is named as pMAK701. *Escherichia coli* bacteria AJ 12759 possessing the plasmid pMAK701 was deposited to National Institute of Bioscience and Human Technology, Agency of Industrial Science and Technology (1–3, Higashi 1-chome, Tsukuba-shi, Ibaraki-ken, Japan; zip code 305) on Jan. 11, 1993 under the deposition number of FERM P-13364, transferred from the original deposition to international deposition based on Budapest Treaty on Jan. 11, 1994 and has been deposited as Deposition No. FERM BP-4533.

By the way, the plasmid containing the DNA fragment having the base sequence described in the sequence table, SEQ ID No:5 is not deposited in the Example 2. However, it will be obvious to those skilled in the art to introduce site-directed mutagenisis to the gene by a method, for example, a PCR method or a method of utilizing a U-containing single stranded DNA. Accordingly, a plasmid containing a DNA fragment having the base sequence described in the sequence table, SEQ ID No:5 can be prepared easily using pMAK701 as the starting material.

(2) Preparation of K-protein gene disrupted strain

Figure 1:
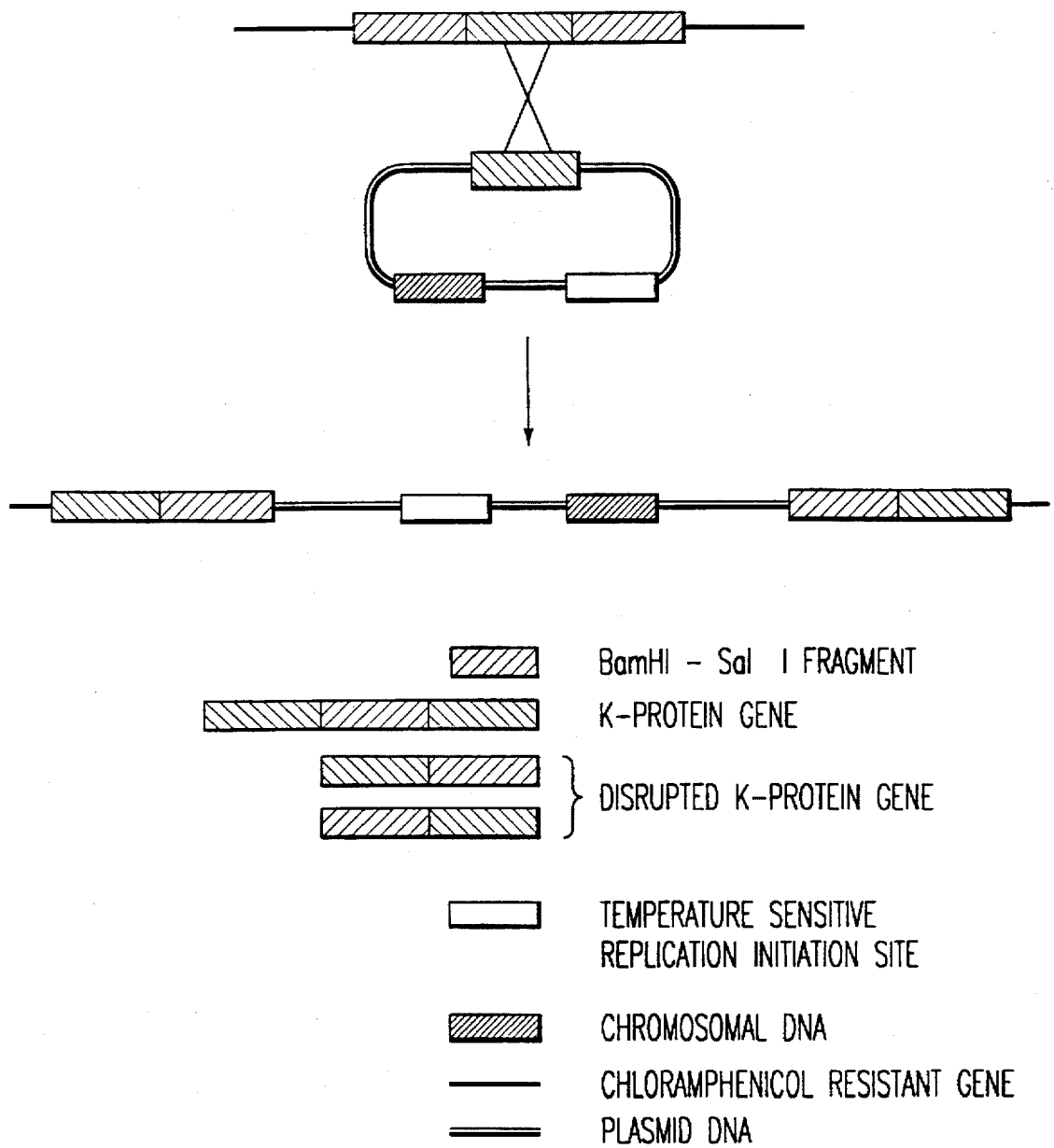
FIG. 1: schematic view for the gene disruption by homologous recombination.

From the DNA fragment containing the K-protein mutant gene obtained in Example 3 (1), BamHI-SalI fragment having about 650 base pair length was cut out and ligated with the BamHI-SalI site of the vector pHSC4 having a temperature sensitive replication initiation point (Sugimoto, et al., French Patent Laid-Open Publication No. 2667875/ 1992) to prepare a plasmid for gene disruption pMAK705. pMAK705 was introduced into *Brevibacterium lactofermentum* 2256 (ATCC 13869) given with AEC (S-(2-aminoethyl)-n-cystein) resistance (referred to herein as AEC$^r$ 2256 strain) by way of an electric pulse method (Sugimoto et al., Japanese Patent Laid-Open Publication 90-207791). The obatined transformants were cultivated at a plasmid replication inhibiting temperature so that the chromosomal K-protein gene was disrupted by homologous recombination at the Bam HI-Sal I region of the K-protein gene. A view for the mechanism of gene disruption is shown in FIG. 1. The BamHI-SalI fragment of the mutant K-protein gene corresponds to the region from BamHI site (nucleotide number 1156–1161 in SEQ ID No:7) to SalI site (1704–1709) of the sequence shown in SEQ ID No:7, which is present in ORF (Open Reading Frame) shown in SEQ ID No:5. Accordingly, one of two copies of disrupted K-protein genes resulting from the homologous recombination depletes most of 3' side of ORF while the other depletes most of 5' side of ORF. Details of the experiment will be described.

AEC$^r$ 2256 strain possessing pMAK705 was cultivated in a CM2G medium containing 5 μg/ml of chloramphenicol overnight. The culture broth was diluted with a CM2G medium to 10$^{-3}$ and 100 μl thereof was spread on a CM2G plate containing 5 μg/ml of chloramphenicol. Cultivation was performed at 34° C. (replication inhibitive temperature) overnight to select chloramphenicol resistant bacteria. Cell surface layer fractions for two chloramphenicol resistant strains thus obtained were prepared by the method as described in Example 1 were subjected to SDS-polyacrylamide gel electrophoresis and deficiency of the K-protein was confirmed. Thus prepared two strains of K-protein-deficient strain were named as AJ 12760 and AJ 12956, respectively. The growing rate of the AJ 12760 and AJ 12956 were equal with that of the AEC$^r$ 2256 strain.

The K-protein-deficient strain AJ 12760 was deposited to National Institute of Bioscience and Human Technology, Agency of Industrial Science and Technology (1–3, Higashi 1-chome, Tsukuba-shi, Ibaraki-ken, Japan; zip code 305)on Jan. 11, 1993 as FERM P-13365 and transferred on Jan. 11, 1994 from the original deposition to international deposition based on the Budapest Treaty and deposited with a deposition No. FERM BP-4534. Further, K-protein-deficient strain AJ 12956 was internationally deposited based on the Budapest Treaty on Jan. 11, 1994 to National Institute of Bioscience and Human Technology, Agency of Industrial Science and Technology (1–3, Higashi 1-chome, Tsukuba-shi, Ibaraki-ken, Japan; zip code 305) with the deposition No. as FERM BP-4532.

(3) Ammonium incorporation activity of K-protein-deficient strain

Figure 2:
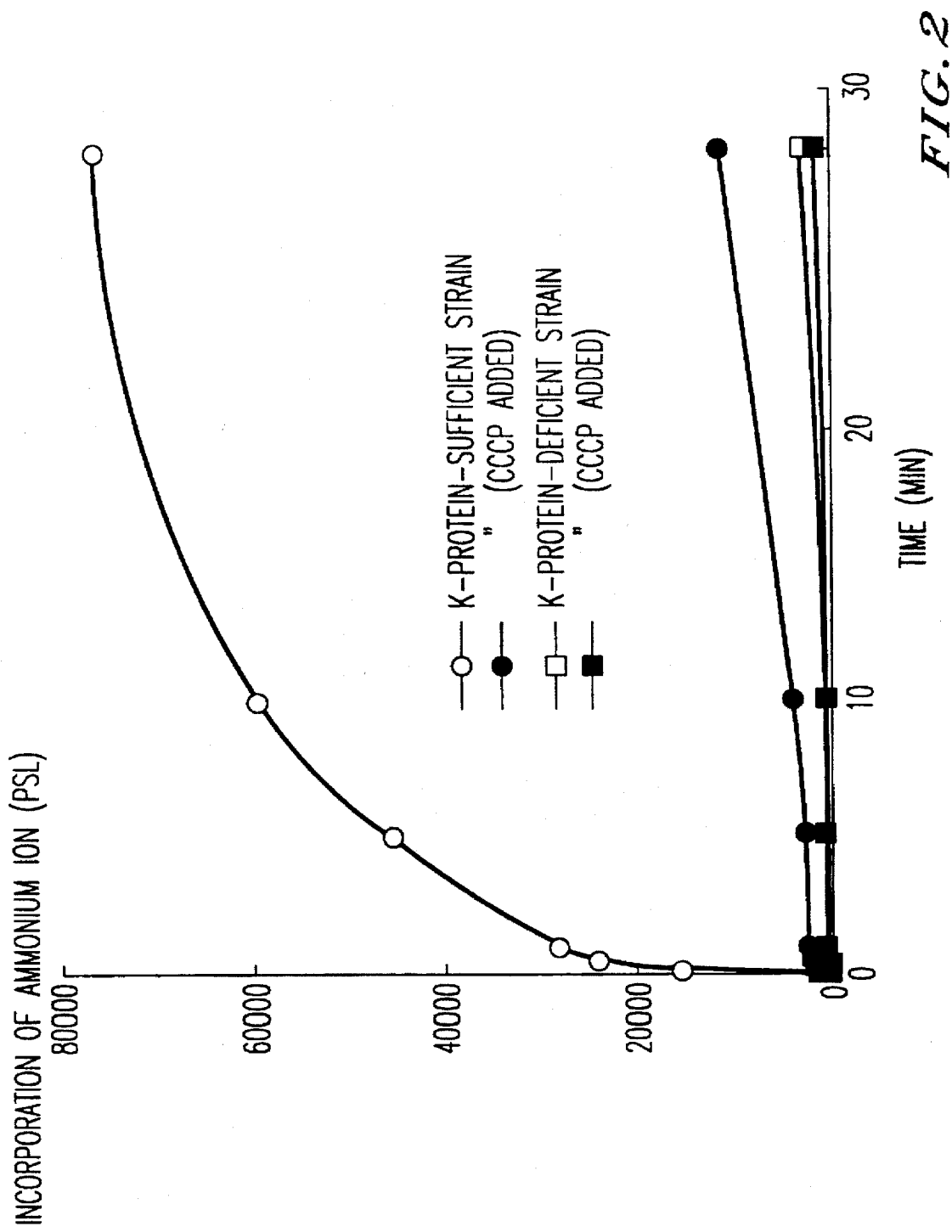
FIG. 2: shows contribution of K-protein to incorporation of ammonium ions.

When ammonium incorporation activity of the K-protein-deficient strain AJ 12760 prepared in (1) above was measured, a remarkable reduction was observed as compared with the AEC$^r$ 2256 strain as shown in FIG. 2. Measurement of ammonium incorporation was performed using $^{14}C$ labeled methyl ammonium, an analogue of ammonium ions, as a substrate and according to a rapid filtration method (A. Jayakumar, et al., Analytical Biochemistry, 135 (1983) 475–478). From the result, it has been proved that the K-protein is a novel cell surface layer protein contributing to the incorporation of nutrients in Coryneform bacteria.

Details for the experiment measuring ammonium incorporation activity of the K-protein-deficient strain AJ 12760 are shown below. Bacterial cells for which the incorporation activity was to be measured were inoculated from a CM2G agar plate to a CM2G liquid medium and cultivated at 30° for overnight. After cooling the culture broth in a iced water, cells were collected and washed twice with a previously ice cooled buffer B (50 mM Tris-HCl, pH 6.8, 100 mM NaCl) and suspended in a buffer B to give a density of $2.0 \times 10^8$ cells/ml. 100 μl of cell suspension was placed in a well of Multi-Screen HA manufactured by Milipore Co. to which glucose was added to a final concentration of 10 mM as an energy source and kept at a temperature of 30° C. for 5 min. In this course, CCCP (carbonylcyanide m-chlorophenylhydrazone (manufactured by Sigma Co.)) was present together as a decoupling agent if necessary (final concentration at 20 μM).

The ammonia incorporating reaction was started by adding $^{14}C$-labelled methyl ammonium to each of wells to a final concentration of 20 μM. After keeping a temperature at 25° C. for a predetermined period of time, the reaction solution was rapidly removed from each of the wells by sucking to terminate the reaction. After sucking of reaction solution cells held on the Multi-Screen HA membrane was washed with a buffer C (50 mM Tris-HCl, pH 6.8, 1M NaCl) and, after drying the membrane, $^{14}C$ radioactivity incorporated into the cells was mesured by using a Sio-imaging Analyzer (BAS-2000, manufactured by Fuji Photographic Film Inc.)

EXAMPLE 4

Precipitation property of K-protein-deficient strain

Precipitation property of the K-protein-deficient strain in the culture medium was evaluated. AJ 12760 and AJ 12956 as the K-protein gene disrupted strain and the YSR strain as the K-protein-deficient mutant strain were used as the K-protein-deficient strain. In addition, *Brevibacterium lactofermentum* 2256 (ATCC 13869) and AEC$^r$ 2256 as the K-protein-sufficent strain were used as a control. Each strain of AJ 12760, AJ 12956, YSR, 2256 and ACE$^r$ 2256 was cultivated overnight in CM2G plate containing 20 μg/ml of chloramphenicol and one platinum loop of each cells (amount corresponding to 1/40 of a plate) was inoculated to a main liquid culture medium and cultivated at 31.5° C. for 24 hours. For the main liquid culture medium, 20 ml of a liquid culture medium of the following composition was placed in a 500 ml volume Sakaguchi flask, adjusted to pH 8.0 by using KOH, heat sterilized at 115° C. for 10 min and then CaCO$_3$ sterilized under dry heating at 200° C. for three hours was added additionally.

TABLE 3

Composition for Culture Medium

| Ingredient | Amount of blend |
|---|---|
| Glucose or sucrose | 10 g/100 mL |
| (NH$_4$)$_2$SO$_4$ | 5.5 g/100 mL |
| KH$_2$PO$_4$ | 0.1 g/100 mL |
| MgSO$_4$.7H$_2$O | 0.1 g/100 mL |
| FeSO$_4$.7H$_2$O | 0.001 g/100 mL |
| MnSO$_4$.4H$_2$O | 0.001 g/100 mL |
| "Mame no" (hydrolyzate of soybean protein)* | 0.05 g/100 ml (as tatal nitrogen) |
| Vitamin B1 hydrochloride | 200 g/L |
| Biotin | 500 g/L |
| GD-113 (defoamer: manufactured by Nippon Yushi Co.) | 0.002 mL/100 mL |
| CaCO$_3$ (sterilized by dry heating at 200 C. for 3 hrs) | 5.0 g/100 mL |

The "mame no" contains 3.49 g nitrogen/100 ml

Cultivation for each of the K-protein disrupted strain, K-protein deficient mutant and K-protein-sufficent strain was performed by a duplicate system using a medium added with glucose and a medium added with sucrose. Table 4 shows a carbon source and pH measured after cultivation for each of cultivation lots (specimen No.).

TABLE 4

| Specimen No. | Strain | Carbon Source | pH |
|---|---|---|---|
| 1 | 2256 | glucose | 6.48 |
| 2 | 2256 | sucrose | 6.30 |
| 3 | YSR | glucose | 6.28 |
| 4 | YSR | sucrose | 6.18 |
| 5 | AEC$^r$2256 | glucose | 6.20 |
| 6 | AEC$^r$2256 | sucrose | 6.32 |
| 7 | AJ 12760 | glucose | 5.93 |
| 8 | AJ 12760 | sucrose | 5.74 |
| 9 | AJ 12956 | glucose | 5.88 |
| 10 | AJ 12956 | sucrose | 5.78 |
| 11 | 2256 | glucose | 6.28 |
| 12 | 2256 | sucrose | 6.20 |
| 13 | YSR | glucose | 6.24 |
| 14 | YSR | sucrose | 6.14 |
| 15 | AEC$^r$2256 | glucose | 6.26 |
| 16 | AEC$^r$2256 | sucrose | 6.38 |
| 17 | AJ 12760 | glucose | 5.99 |
| 18 | AJ 12760 | sucrose | 5.79 |
| 19 | AJ 12956 | glucose | 5.90 |
| 20 | AJ 12956 | sucrose | 5.77 |

Among the dual cultivation lots cultivated in the glucose added culture and the sucrose added culture, a precipitation test was applied for one system (specimen Nos. 1–10) while leaving the culture medium as it was after cultivation and for the other system (specimen Nos. 11–20) while adjusting pH to 4.0 of the culture medium after cultivation. pH 4.0 is a condition in a case of usually purifying L-lysin-HCl by ion exchange chromatography.

A precipitation test was conducted as described below. Each 15 mL culture medium after cultivation was transferred to a test tube of 15 mm inner diameter and stood still to spontaneously precipitate cells. After elapse of a predetermined period of time, a position at the boundary between supernatants resulting from the precipitation of the cells and the precipitation portion in which the cells were suspended was measured to calculate the relative precipitation degree by the formula described below, while assuming the ratio (%) of the distance b which is from the surface of medium to the boundary to the hight a of the surface of medium as "supernatant ratio". The cell concentration was measured based on optical absorption at 562 nm ($OD_{562}$) when the culture medium was diluted by 26 times. Further, the height a of the surface of medium when 15 mL of the medium was transferred to a test tube was 9 cm. The dry cell weight was calculated by conversion from $OD_{562}$ in accordance with a previously prepared conversion equation.

1, 3, 5, 7 and 9 in FIG. 3, for the specimen 2, 4, 6, 8 and 10 in FIG. 4, for the specimens 11, 13, 15, 17 and 19 in FIG. 5 and for the specimens 12, 14, 16, 18 and 20 in FIG. 6.

TABLE 5

| specimen No. | total cell OD | 0 b (mm) | 0 sup OD | 10 min b (mm) | 10 min sup OD | 30 min b (mm) | 30 min sup OD | 60 mim b (mm) | 60 mim sup OD | 180 mim b (mm) | 180 mim sup OD | 23 hr b (mm) | 23 hr sup OD |
|---|---|---|---|---|---|---|---|---|---|---|---|---|---|
| 1 | 1.30 | 0 | 1.30 | 0 | 1.20 | 0 | 1.15 | 0 | 1.18 | 0 | 1.08 | 0 | 1.03 |
| 2 | 1.30 | 0 | 1.30 | 0 | 1.20 | 0 | 1.11 | 0 | 1.11 | 0 | 0.96 | 0 | 0.91 |
| 3 | 1.21 | 0 | 1.21 | 0 | 1.00 | 70 | 1.05 | 65 | 1.08 | 30 | 0.56 | 65 | 0.47 |
| 4 | 1.20 | 0 | 1.20 | 0 | 1.08 | 70 | 1.02 | 70 | 1.01 | 66 | 0.74 | 63 | 0.65 |
| 5 | 0.51 | 0 | 0.51 | 0 | 0.50 | 0 | 0.49 | 0 | 0.50 | 0 | 0.42 | 5 | 0.15 |
| 6 | 0.46 | 0 | 0.46 | 0 | 0.44 | 0 | 0.42 | 0 | 0.42 | 0 | 0.35 | 4 | 0.22 |
| 7 | 1.05 | 0 | 1.05 | 45 | 0.62 | 50 | 0.52 | 55 | 0.48 | 60 | 0.28 | 55 | 0.17 |
| 8 | 1.05 | 0 | 1.05 | 55 | 0.70 | 52 | 0.54 | 50 | 0.47 | 55 | 0.25 | 60 | 0.32 |
| 9 | 1.10 | 0 | 1.10 | 50 | 0.90 | 45 | 0.65 | 45 | 0.55 | 50 | 0.38 | 50 | 0.31 |
| 10 | 1.07 | 0 | 1.07 | 50 | 0.72 | 50 | 0.53 | 30 | 0.47 | 65 | 0.29 | 55 | 0.33 |

TABLE 6

| specimen No. | total cell OD | 0 b (mm) | 0 sup OD | 10 min b (mm) | 10 min sup OD | 30 min b (mm) | 30 min sup OD | 60 mim b (mm) | 60 mim sup OD | 180 mim b (mm) | 180 mim sup OD | 23 hr b (mm) | 23 hr sup OD |
|---|---|---|---|---|---|---|---|---|---|---|---|---|---|
| 11 | 1.25 | 0 | 1.25 | 0 | 1.20 | 0 | 0.00 | 80 | 1.18 | 80 | 1.05 | 80 | 1.15 |
| 12 | 1.25 | 0 | 1.25 | 0 | 1.25 | 0 | 0.00 | 80 | 1.20 | 75 | 1.08 | 75 | 1.10 |
| 13 | 1.10 | 0 | 1.10 | 0 | 1.15 | 60 | 1.05 | 65 | 1.04 | 70 | 0.91 | 70 | 0.85 |
| 14 | 1.05 | 0 | 1.05 | 0 | 1.05 | 0 | 0.00 | 70 | 1.01 | 40 | 0.89 | 70 | 0.92 |
| 15 | 0.44 | 0 | 0.44 | 0 | 0.42 | 70 | 0.37 | 65 | 0.34 | 67 | 0.32 | 70 | 0.28 |
| 16 | 0.44 | 0 | 0.44 | 0 | 0.44 | 60 | 0.41 | 60 | 0.39 | 60 | 0.38 | 65 | 0.29 |
| 17 | 1.25 | 0 | 1.25 | 40 | 0.08 | 60 | 0.05 | 60 | 0.04 | 65 | 0.05 | 75 | 0.03 |
| 18 | 1.15 | 0 | 1.15 | 40 | 0.05 | 50 | 0.05 | 55 | 0.04 | 57 | 0.05 | 60 | 0.03 |
| 19 | 1.00 | 0 | 1.00 | 30 | 0.05 | 48 | 0.05 | 50 | 0.04 | 50 | 0.05 | 60 | 0.04 |
| 20 | 1.00 | 0 | 1.00 | 40 | 0.05 | 60 | 0.05 | 65 | 0.03 | 70 | 0.05 | 75 | 0.03 |

$$\text{(Relative precipitation degree)} = \frac{\text{(Cell density in precipitation portion)}}{\text{(Total cell concentration)}} \times 100$$

$$\text{(Cell density in precipitation portion)} = \frac{\text{(dry cell weight in homogeneous state)} \times 100 - \text{(dry cell weight in supernatant)} \times \text{(supernatant ratio)}}{100 - \text{(supernatant ratio)}}$$

$$\text{(Supernatant ratio)} = (b/a) \times 100$$

a: height of the surface of medium (that is, total height of the supernatant portion and the precipitation protion)

b: distance from the surface of medium to the boundary (that is, a numerical value obtained by subtracting the boundary height from a)

$$\text{(Dry cell weight)} = 1.586(OD_{562})^3 - 1.446(OD_{562})^2 - 1.396(OD_{562}) - 0.013$$

The total cell density (total cell OD), the distance from the surface of medium To the boundary (b), the height of the surface of medium (a) and the cell density in the supernatant (supernatant OD) in each of the cultivation lots were measured immediately after, 10 min after, 30 min after, 60 min after, 180 min after and 23 hr after transferring the culture medium to the test tube and the results are shown in Table 5 and Table 6. The value of relative precipitation degree of each time is calculated and the results are shown in Table 7 and Table 8. Further, the change of the relative precipitation degree with elapse of time was illustrated for the specimens

TABLE 7

| specimen No. | Relative precipitation degree | | | | | |
|---|---|---|---|---|---|---|
| | 0 | 10 mim | 30 min | 60 min | 180 mim | 23 hr |
| 1 | 100 | 100 | 100 | 100 | 100 | 100 |
| 2 | 100 | 100 | 100 | 100 | 100 | 100 |
| 3 | 100 | 100 | 100 | 203 | 145 | 444 |
| 4 | 100 | 100 | 247 | 254 | 317 | 298 |
| 5 | 100 | 100 | 100 | 100 | 100 | 104 |
| 6 | 100 | 100 | 100 | 100 | 100 | 102 |
| 7 | 100 | 168 | 197 | 229 | 298 | 263 |
| 8 | 100 | 216 | 223 | 219 | 285 | 340 |
| 9 | 100 | 158 | 180 | 189 | 232 | 238 |
| 10 | 100 | 188 | 214 | 221 | 458 | 277 |

TABLE 8

| specimen No. | Relative precipitation degree | | | | | |
|---|---|---|---|---|---|---|
| | 0 | 10 mim | 30 mim | 60 mim | 180 mim | 23 hr |
| 11 | 100 | 100 | 100 | 171 | 282 | 633 |
| 12 | 100 | 100 | 100 | 178 | 249 | 600 |
| 13 | 100 | 100 | 117 | 126 | 193 | 380 |
| 14 | 100 | 100 | 100 | 138 | 126 | 567 |
| 15 | 100 | 100 | 177 | 175 | 203 | 600 |
| 16 | 100 | 100 | 120 | 133 | 140 | 533 |
| 17 | 100 | 170 | 268 | 269 | 312 | 475 |
| 18 | 100 | 187 | 239 | 280 | 298 | 340 |

TABLE 8-continued

| specimen | Relative precipitation degree | | | | | |
|---|---|---|---|---|---|---|
| No. | 0 | 10 min | 30 min | 60 min | 180 min | 23 hr |
| 19 | 100 | 153 | 225 | 239 | 238 | 340 |
| 20 | 100 | 170 | 265 | 313 | 370 | 475 |

From the foregoing results, it has been found that cells were precipitated in a short period of time (10–30 min) irrespective of the kind of the carbon source in the culture medium and adjustment and non-adjustment for the pH value of the culture medium after the completion of the cultivation for the K-protein gene disrupted strain AJ 12760 strain AJ 12956. Further, it has been found that cells of the K-protein deficent mutant YSR were precipitated in a short period of time in the same manner as the K-protein gene disrupted strain when they are cultivated by using sucrose as the carbon source and stood still after the completion of the cultivation without adjusting pH. On the contrary, cells of the AEC$^r$ 2256 and 2256 as the K-protein-sufficient strains were not substantially precipitated even if the culture medium was stood still 30 min after the completion of the cultivation. Particularly, precipitation of the cells was not recognized even after 23 hours if they were stood still without adjusting the pH of the culture medium.

For the precipitation degree of the cells, measurement for the precipitation constant of cell aggregation products give the same result as the relative precipitation degree measured as described above.

INDUSTRIAL APPLICABILITY

The present invention provides a novel cell surface layer protein that contributes to the incorporation of nutrients in Coryneform bacteria and the gene thereof, as well as provides the transformant obtained by introduction and amplifying the gene in the cells of Coryneform bacteria. Further, it also enables to improve a process for producing L-amino acid by a fermentation method using Coryneform bacteria having an activity to produce L-amino acid as a host for the transformant and improving the process for producing the L-amino acid by the fermentation method using the host bacteria.

Furthermore, the present invention provides novel Coryneform bacteria being deficient in the cell surface layer protein and having a aggregating property, thereby enabling to save energy in the production of L-amino acid by utilizing them.

We claim:

1. An isolated DNA fragment containing a gene coding for a cell surface layer protein derived from *Brevibacterium lactofermentum* having the following two sequences of:
   (1) Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-Asp-Gln-Ala-Ala-Arg-Glu-Leu-Phe-Leu-Asp-Trp-Asp-Thr (SEQ ID NO:1) and:
   (2) Asn-Lys-Thr-Asp-Phe-Asp-Phe-Ala-Ile-Glu-Leu-Tyr-Asp-Val-Leu-Tyr-Thr-Asp-Ala-Asp-Ile-Ser-Gly-Asp-Ala-Pro-Leu-Leu-Ala-Pro-Ala-Tyr-Lys (SEQ ID NO:2)
in the molecule, and having a molecular weight of about 63,000 dalton.

2. A recombinant DNA obtained by ligating the DNA fragment defined in claim 1 with a vector which replicates in a cell of Coryneform bacteria.

3. A Coryneform transformant comprising the DNA fragment of claim 1.

4. A method for producing a useful substance by a fermentation process which comprises cultivating a transformant defined in claim 3 having an activity to produce a useful substance in a culture medium, forming and accumulating said useful substance in the culture medium and collecting said useful substance from the culture medium, wherein said useful substance is selected from the group consisting of amino acids, nucleic acids and foreign proteins.

5. A method as defined in claim 4, wherein the useful substance is an L-amino acid.

* * * * *